(12) United States Patent
Bauer et al.

(10) Patent No.: US 8,071,536 B2
(45) Date of Patent: Dec. 6, 2011

(54) MUTANT DNA POLYMERASES WITH IMPROVED PYROPHOSPHOROLYSIS ACTIVATED POLYMERIZATION (PAP) ABILITY

(75) Inventors: Keith A Bauer, San Rafael, CA (US); David Harrow Gelfand, Oakland, CA (US)

(73) Assignee: Roche Molecular System, Inc., Pleasanton, CA (US)

( * ) Notice: Subject to any disclaimer, the term of this patent is extended or adjusted under 35 U.S.C. 154(b) by 215 days.

(21) Appl. No.: 12/324,491

(22) Filed: Nov. 26, 2008

(65) Prior Publication Data

US 2009/0155802 A1 Jun. 18, 2009

Related U.S. Application Data

(60) Provisional application No. 60/990,847, filed on Nov. 28, 2007.

(51) Int. Cl.
| | |
|---|---|
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |

(52) U.S. Cl. ......... 514/1.1; 530/327; 530/328; 530/329; 530/330

(58) Field of Classification Search ........................ None
See application file for complete search history.

(56) References Cited

U.S. PATENT DOCUMENTS 6,329,178 B1 * 12/2001 Patel et al. ................. 435/91.1
7,148,049 B2 * 12/2006 Schoenbrunner et al. .... 435/194
7,572,581 B2 * 8/2009 Gelfand et al. .................. 435/6
7,745,125 B2 * 6/2010 Gelfand et al. .................. 435/6
2004/0005599 A1 1/2004 Schoenbrunner et al.

FOREIGN PATENT DOCUMENTS

| WO | WO 03/095664 | 11/2003 |
| WO | WO 2008/046612 | 4/2008 |
| WO | WO 2009/010251 | 1/2009 |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976), pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Deng et al. Characterization of five novel dehydration-responsive homeodomain leucine zipper genes from the resurrection plant Craterostigma plantagineum. Plant Molecular Biology. 2002. vol. 49, pp. 601-610.*

* cited by examiner

*Primary Examiner* — Marcela M Cordero Garcia
(74) *Attorney, Agent, or Firm* — Rhea C. Nersesian

(57) ABSTRACT

Disclosed are mutant DNA polymerases having improved extension rates relative to a corresponding, unmodified polymerase. The mutant polymerases are useful in a variety of disclosed primer extension methods. Also disclosed are related compositions, including recombinant nucleic acids, vectors, and host cells, which are useful, e.g., for production of the mutant DNA polymerases.

22 Claims, 12 Drawing Sheets

```
Tth     RELTKL  KNTYVDPLP
Tca     RELTKL  KNTYVDPLP
Z05     RELTKL  KNTYVDPLP
Taq     RELTKL  KSTYIDPLP
Tfl     RELTKL  KNTYIDPLP
Tfi     RELMKL  KSTYIDPLP
Sps17   RELMKL  KSTYIDPLP
Dra     RELDKL  RGTYLDPIP         *
HspB7   RELSKL  RSTYADALP
Bst     RQLGKL  QSTYIEGLL
Bca     RQLGKL  QSTYIEGLL
Eco     RGLAKL  KSTYTDKLP
Tma     RKIQKL  KSTYIDALP
Tne     RKILKL  KSTYIDTLP
Taf     RKYQKL  KSTYIDSIP
HspA    RTLAKL  KSTYVDALP
CS5     RKIQKL  KSTYIDALP
CS6     RKIQKL  KSTYIDALP
T7      LMIQKRIGQSAEGDKAW
Cons    R---KL--KL----TY----
```

Figure 1

```
  1 MKAMLPLFEP KGRVLLVDGH HLAYRTFFAL KGLTTSRGEP VQAVYGFAKS
 51 LLKALKEDGY KAVFVVFDAK APSFRHEAYE AYKAGRAPTP EDFPRQLALI
101 KELVDLLGFT RLEVPGFEAD DVLATLAKKA EREGYEVRIL TADRDLYQLV
151 SDRVAVLHPE GHLITPEWLW EKYGLKPEQW VDFRALVGDP SDNLPGVKGI
201 GEKTALKLLK EWGSLENILK NLDRVKPESV RERIKAHLED LKLSLELSRV
251 RSDLPLEVDF ARRREPDREG LRAFLERLEF GSLLHEFGLL EESEPVGYRI
301 VKDLVEFEKL IEKLRESPSF AIDLETSSLD PFDCDIVGIS VSFKPKEAYY
351 IPLHHRNAQN LDEKEVLKKL KEILEDPGAK IVGQNLKFDY KVLMVKGVEP
401 VPPYFDTMIA AYLLEPNEKK FNLDDLALKF LGYKMTSYQE LMSFSFPLFG
451 FSFADVPVEK AANYSCEDAD ITYRLYKTLS LKLHEADLEN VFYKIEMPLV
501 NVLARMELNG VYVDTEFLKK LSEEYGKKLE ELAEEIYRIA GEPFNINSPK
551 QVSRILFEKL GIKPRGKTTK TGDYSTRIEV LEELAGEHEI IPLILEYRKI
601 QKLKSTYIDA LPKMVNPKTG RIHASFNQTG TATGRLSSSD PNLQNLPTKS
651 EEGKEIRKAI VPQDPNWWIV SADYSQIELR ILAHLSGDEN LLRAFEEGID
701 VHTLTASRIF NVKPEEVTEE MRRAGKMVNF SIIYGVTPYG LSVRLGVPVK
751 EAEKMIVNYF VLYPKVRDYI QRVVSEAKEK GYVRTLFGRK RDIPQLMARD
801 RNTQAEGERI AINTPIQGTA ADIIKLAMIE IDRELKERKM RSKMIIQVHD
851 ELVFEVPNEE KDALVELVKD RMTNVVKLSV PLEVDVTIGK TWS
```

Figure 2A

```
  1    ATGAAAGCTA TGTTACCATT ATTCGAACCC AAAGGCCGGG TCCTCCTGGT
 51    GGACGGCCAC CACCTGGCCT ACCGCACCTT CTTCGCCCTG AAGGGCCTCA
101    CCACGAGCCG GGGCGAACCG GTGCAGGCGG TTTACGGCTT CGCCAAGAGC
151    CTCCTCAAGG CCCTGAAGGA GGACGGGTAC AAGGCCGTCT TCGTGGTCTT
201    TGACGCCAAG GCCCCTTCCT TCCGCCACGA GGCCTACGAG GCCTACAAGG
251    CAGGCCGCGC CCCGACCCCC GAGGACTTCC CCCGGCAGCT CGCCCTCATC
301    AAGGAGCTGG TGGACCTCCT GGGGTTTACT CGCCTCGAGG TTCCGGGCTT
351    TGAGGCGGAC GACGTCCTCG CCACCCTGGC CAAGAAGGCG GAAAGGGAGG
401    GGTACGAGGT GCGCATCCTC ACCGCCGACC GGGACCTTTA CCAGCTCGTC
451    TCCGACCGCG TCGCCGTCCT CCACCCCGAG GGCCACCTCA TCACCCCGGA
501    GTGGCTTTGG GAGAAGTACG GCCTTAAGCC GGAGCAGTGG GTGGACTTCC
551    GCGCCCTCGT GGGGGACCCC TCCGACAACC TCCCCGGGGT CAAGGGCATC
601    GGGGAGAAGA CCGCCCTCAA GCTCCTCAAG GAGTGGGGAA GCCTGGAAAA
651    TATCCTCAAG AACCTGGACC GGGTGAAGCC GGAAAGCGTC CGGGAAAGGA
701    TCAAGGCCCA CCTGGAAGAC CTTAAGCTCT CCTTGGAGCT TTCCCGGGTG
751    CGCTCGGACC TCCCCCTGGA GGTGGACTTC GCCCGGAGGC GGGAGCCTGA
801    CCGGGAAGGG CTTCGGGCCT TTTTGGAGCG CTTGGAGTTC GGCAGCCTCC
851    TCCACGAGTT CGGCCTTCTA GAGGAGTCCG AACCCGTTGG GTACCGTATA
901    GTTAAAGACC TGGTTGAATT TGAAAAACTC ATAGAGAAAC TGAGAGAATC
951    TCCTTCGTTC GCTATCGATT TGGAAACTAG TTCCCTCGAT CCTTTCGACT
1001   GCGACATTGT CGGTATCTCT GTGTCTTTCA AACCAAAGGA AGCGTACTAC
1051   ATACCACTCC ATCATAGAAA CGCCCAGAAC CTGGACGAAA AAGAGGTTCT
1101   GAAAAGCTC AAAGAAATTC TGGAGGACCC CGGAGCAAAG ATCGTTGGTC
1151   AGAATTTGAA ATTCGATTAC AAGGTGTTGA TGGTGAAGGG TGTTGAACCT
1201   GTTCCTCCTT ACTTCGACAC GATGATAGCG GCTTACCTTC TTGAGCCGAA
1251   CGAAAAGAAG TTCAATCTGG ACGATCTCGC ATTGAAATTT CTTGGATACA
1301   AAATGACATC TTACCAAGAG CTCATGTCCT TCTCTTTTCC GCTGTTTGGT
```

Figure 2B-1

```
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT CAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

Figure 2B-2

```
  1  MKAMLPLFEP KGRVLLVDGH HLAYRTFFAL KGLTTSRGEP VQAVYGFAKS
 51  LLKALKEDGY KAVFVVFDAK APSFRHEAYE AYKAGRAPTP EDFPRQLALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
251  RSDLPLEVDF ARRREPDREG LRAFLERLEF GSLLHEFGLL EESEPVGYRI
301  VKDLVEFEKL IEKLRESPSF AIALATSSLD PFDCDIVGIS VSFKPKEAYY
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
852  ELVFEVPNEE KDALVELVKD RMTNVVKLSV PLEVDVTIGK TWS
```

Figure 3A

```
   1  ATGAAAGCTA TGTTACCATT ATTCGAACCC AAAGGCCGGG TCCTCCTGGT
  51  GGACGGCCAC CACCTGGCCT ACCGCACCTT CTTCGCCCTG AAGGGCCTCA
 101  CCACGAGCCG GGGCGAACCG GTGCAGGCGG TTTACGGCTT CGCCAAGAGC
 151  CTCCTCAAGG CCCTGAAGGA GGACGGGTAC AAGGCCGTCT TCGTGGTCTT
 201  TGACGCCAAG GCCCCTTCCT TCCGCCACGA GGCCTACGAG GCCTACAAGG
 251  CAGGCCGCGC CCCGACCCCC GAGGACTTCC CCCGGCAGCT CGCCCTCATC
 301  AAGGAGCTGG TGGACCTCCT GGGGTTTACT CGCCTCGAGG TTCCGGGCTT
 351  TGAGGCGGAC GACGTCCTCG CCACCCTGGC CAAGAAGGCG GAAAGGGAGG
 401  GGTACGAGGT GCGCATCCTC ACCGCCGACC GGGACCTTTA CCAGCTCGTC
 451  TCCGACCGCG TCGCCGTCCT CCACCCCGAG GGCCACCTCA TCACCCCGGA
 501  GTGGCTTTGG GAGAAGTACG GCCTTAAGCC GGAGCAGTGG GTGGACTTCC
 551  GCGCCCTCGT GGGGGACCCC TCCGACAACC TCCCCGGGGT CAAGGGCATC
 601  GGGGAGAAGA CCGCCCTCAA GCTCCTCAAG GAGTGGGGAA GCCTGGAAAA
 651  TATCCTCAAG AACCTGGACC GGGTGAAGCC GGAAAGCGTC CGGGAAAGGA
 701  TCAAGGCCCA CCTGGAAGAC CTTAAGCTCT CCTTGGAGCT TTCCCGGGTG
 751  CGCTCGGACC TCCCCCTGGA GGTGGACTTC GCCCGGAGGC GGGAGCCTGA
 801  CCGGGAAGGG CTTCGGGCCT TTTTGGAGCG CTTGGAGTTC GGCAGCCTCC
 851  TCCACGAGTT CGGCCTTCTA GAGGAGTCCG AACCCGTTGG GTACCGTATA
 901  GTTAAAGACC TGGTTGAATT TGAAAAACTC ATAGAGAAAC TGAGAGAATC
 951  TCCTTCGTTC GCGATCGCTC TTGCGACTAG TTCCCTCGAT CCTTTCGACT
1001  GCGACATTGT CGGTATCTCT GTGTCTTTCA ACCAAAGGA AGCGTACTAC
1051  ATACCACTCC ATCATAGAAA CGCCCAGAAC CTGGACGAAA AAGAGGTTCT
1101  GAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
```

Figure 3B-1

```
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AAGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

MUTANT DNA POLYMERASES WITH IMPROVED PYROPHOSPHOROLYSIS ACTIVATED POLYMERIZATION (PAP) ABILITY

CROSS REFERENCE TO RELATED APPLICATIONS

This application claims the benefit of U.S. Provisional Patent Application No. 60/990,847 filed on Nov. 28, 2007, the disclosure of which is hereby incorporated by reference.

FIELD OF THE INVENTION

The present invention lies in the field of DNA polymerases and their use in various applications, including pyrophosphorolysis activated polymerization.

BACKGROUND OF THE INVENTION

Pyrophosphorolysis activated polymerization (PAP) is a PCR method in which the primer(s) end in an extension terminator which must be removed by pyrophosphorolysis before the primer(s) can be extended. "Pyrophosphorolysis" is simply the reverse of the extension of a primed template by DNA polymerase (i.e., the addition of a dNMP residue to the primer strand). In the "forward" reaction (i.e. the extension of a primed template) pyrophosphate is generated and dNTPs are consumed, as dNMPs are added to the 3'-end of the primer. In the "reverse" reaction (i.e. pyrophosphorolysis) pyrophosphate is consumed and dNTPs are generated as dNMPs are removed from the 3'-end of the primer strand. Primed templates ending in a residue which cannot be extended (a "terminator") are expected to be subject to pyrophosphorolysis if the polymerase is able to incorporate the terminator and if pyrophosphate is present. In PAP, the use of these blocked primers allows for rare allele detection because pyrophosphorolysis requires a perfectly matched primer: template complex for maximal rate of terminator removal.

BRIEF SUMMARY OF THE INVENTION

The present invention provides DNA polymerases having improved pyrophosphorolysis activated polymerization ability relative to corresponding unmodified DNA polymerases. The DNA polymerases described herein are useful in the reverse transcription or amplification of polynucleotide templates using primers comprising a terminator nucleotide at the 3'-end. The polymerases of the present invention have utility in, for example, recombinant DNA studies and medical diagnosis of disease involving rare allele detection. In some embodiments, the DNA polymerase comprises the amino acid sequence R-$X_1$-$X_2$-$X_3$-K-L-$X_4$-$X_5$-$X_6$-Y-$X_7$-$X_8$-$X_9$-$X_{10}$-$X_{11}$ (SEQ ID NO:1) wherein $X_1$-$X_5$, and $X_7$-$X_{11}$ are any amino acid, and $X_6$ is not T. In some embodiments, $X_2$ is (L), (I), or (Y); $X_4$ is (K), (R), or (Q); $X_5$ is (N), (S), or (G); $X_6$ is any amino acid except (T); $X_8$ is (D) or (E); $X_{10}$ is (L) or (I); and $X_{11}$ is (P) or (L) (SEQ ID NO:36). In some embodiments, the polymerase has improved nucleic acid extension rate of a blocked primer relative to an otherwise identical DNA polymerase where $X_6$ is T. In some embodiments, $X_1$ is (E), (Q), (G), (K), or (T); $X_3$ is (T), (M), (D), (S), (G), (A), (Q), or (L); $X_7$ is (V), (I), (L), (A), or (T); and $X_9$ is (P), (A), (G), (K), (T), or (S) (SEQ ID NO:37). In some embodiments, $X_6$ is selected from the group consisting of (G), (A), (L), (M), (F), (W), (K), (Q), (E), (S), (P), (V), (I), (C), (Y), (H), (R), (N), and (D) (SEQ ID NO:38). In some embodiments, $X_6$ is S (SEQ ID NO:39).

In some embodiments, the DNA polymerase comprises the amino acid sequence $X_1$-$X_2$-$X_3$-$X_4$-K-$X_5$-$X_6$-$X_7$-$X_8$-$X_9$-$X_{10}$-$X_{11}$-$X_{12}$-$X_{13}$-$X_{14}$-$X_{15}$-$X_{16}$ (SEQ ID NO:2); wherein $X_1$-$X_9$ and $X_{11}$-$X_{16}$ are any amino acid, and $X_{10}$ is not T or A. In some embodiments, $X_1$ is R or L; $X_3$ is L, I, or Y; $X_5$ is R or L; $X_6$ is I or absent; $X_7$ is G or absent; $X_8$ is K, R, or Q; $X_9$ is N, S, or G; $X_{10}$ is any amino acid except T or A; $X_{11}$ is Y or E; $X_{13}$ is D or E; $X_{15}$ is L, I, or A; and $X_{16}$ is P, L, or W (SEQ ID NO:40). In some embodiments, the polymerase has improved nucleic acid extension rate of a blocked primer relative to an otherwise identical DNA polymerase where $X_{10}$ is T or A. In some embodiments, $X_2$ is (E), (Q), (G), (K), (T), or (M); $X_4$ is (T), (M), (D), (S), (G), (A), (Q), or (L); and $X_{12}$ is (V), (I), (L), (A), (T), or (G); and $X_{14}$ is (P), (A), (G), (K), (T), or (S) (SEQ ID NO:41). In some embodiments, $X_{10}$ is selected from the group consisting of (G), (L), (M), (F), (W), (K), (Q), (E), (S), (P), (V), (I), (C), (Y), (H), (R), (N), and (D) SEQ ID NO:42). In some embodiments, $X_{10}$ is S (SEQ ID NO:43).

In some embodiments, the DNA polymerases of the present invention are modified versions of an unmodified polymerase. In its unmodified form, the polymerase generally has PAP ability to extend a blocked primer having a terminator nucleotide at the 3'-end when perfectly matched to a DNA template and includes an amino acid sequence having the following motif: R-$X_1$-$X_2$-$X_3$-K-L-$X_4$-$X_5$-$X_6$-Y-$X_7$-$X_8$-$X_9$-$X_{10}$-$X_{11}$ (SEQ ID NO:24); wherein $X_1$-$X_5$, and $X_7$-$X_{11}$ are any amino acid, and $X_6$ is T. In some embodiments where the polymerase has the motif shown in SEQ ID NO:24, $X_2$ is (L), (I), or (Y); $X_4$ is (K), (R), or (Q); $X_5$ is (N), (S), or (G); $X_6$ is (T); $X_8$ is (D) or (E); $X_{10}$ is (L) or (I); and $X_{11}$ is (P) or (L) (SEQ ID NO:44).

The modified form of the polymerase is further characterized in that it includes an amino acid substitution, relative to its unmodified form, at least at position $X_6$ and has an improved nucleic acid extension rate of a blocked primer relative to its unmodified form. In some embodiments, $X_1$ is (E), (Q), (G), (K), or (T); $X_3$ is (T), (M), (D), (S), (G), (A), (Q), or (L); $X_7$ is (V), (I), (L), (A), or (T); and $X_9$ is (P), (A), (G), (K), (T), or (S) (SEQ ID NO:45). In some embodiments, the amino acid at position $X_6$ is selected from the group consisting of (G), (A), (L), (M), (F), (W), (K), (Q), (E), (S), (P), (V), (I), (C), (Y), (H), (R), (N), and (D) (SEQ ID NO:46). In other embodiments, the amino acid at position $X_6$ is (S) (SEQ ID NO:47).

In some embodiments, where the DNA polymerases in its unmodified form, includes an amino acid sequence having the following motif: $X_1$-$X_2$-$X_3$-$X_4$-K-$X_5$-$X_6$-$X_7$-$X_8$-$X_9$-$X_{10}$-$X_{11}$-$X_{12}$-$X_{13}$-$X_{14}$-$X_{15}$-$X_{16}$ (SEQ ID NO:25); wherein $X_1$-$X_9$ and $X_{11}$-$X_{16}$ are any amino acid, and $X_{10}$ is T or A. In some embodiments, $X_1$ is R or L; $X_3$ is L, I, or Y; $X_5$ is R or L; $X_6$ is I or absent; $X_7$ is G or absent; $X_8$ is K, R, or Q; $X_9$ is N, S, or G; $X_{10}$ is T or A; $X_{11}$ is Y or E; $X_{13}$ is D or E; $X_{15}$ is L, I, or A; and $X_{16}$ is P, L, or W (SEQ ID NO:47).

The modified form of the polymerase is further characterized in that it includes an amino acid substitution, relative to its unmodified form, at least at position $X_{10}$ and wherein the modified form of the polymerase has an improved nucleic acid extension rate of a blocked primer relative to its unmodified form. In some embodiments, $X_{12}$ is (E), (Q), (G), (K), (T), or (M); $X_4$ is (T), (M), (D), (S), (G), (A), (Q), or (L); and $X_{12}$ is (V), (I), (L), (A), (T), or (G); and $X_{14}$ is (P), (A), (G), (K), (T), or (S) (SEQ ID NO:49). In some embodiments, $X_{10}$ is selected from the group consisting of (G), (L), (M), (F), (W), (K), (Q), (E), (S), (P), (V), (I), (C), (Y), (H), (R), (N), and (D) (SEQ ID NO:50). In other embodiments, $X_{10}$ is S (SEQ ID NO:51).

Various DNA polymerases are amenable to mutation according to the present invention. Particularly suitable are thermostable DNA polymerases, including wild-type or naturally occurring thermostable polymerases from various species of thermophilic bacteria, as well as thermostable polymerases derived from such wild-type or naturally occurring enzymes by amino acid substitution, insertion, deletion, or other modification. Exemplary unmodified forms of polymerases include, e.g., CS5 or CS6 DNA polymerase, or a functional DNA polymerase having at least 90% sequence identity thereto. Other suitable unmodified polymerases include, e.g., DNA polymerases from any of the following species of thermophilic bacteria (or a functional DNA polymerase having at least 90% sequence identity to such a polymerase): *Thermus thermophilus, Thermus caldophilus, Thermus* sp. Z05, *Thermus aquaticus, Thermus flavus, Thermus filiformis, Thermus* sp. sps17, *Thermotoga maritima, Thermotoga neapolitana, Thermosipho africanus*. Additional polymerases that are suitable for mutation with the practice of the invention include polymerases having reverse transcriptase activity or any polymerase having PAP ability.

In some embodiments, the unmodified form of the polymerase comprises a chimeric polymerase. In one embodiment, for example, the unmodified form of the chimeric polymerase is CS5 DNA polymerase (SEQ ID NO:20), CS6 DNA polymerase (SEQ ID NO:21), or a polymerase having at least 90% sequence identity to the CS5 DNA polymerase or the CS6 DNA polymerase. In specific variations, the unmodified form of the chimeric polymerase includes one or more amino acid substitutions relative to SEQ ID NO:20 or SEQ ID NO:21 that are selected from G46E, L329A, Q601R, D640G, I669F, S671F, and E678G. For example, the unmodified form of the mutant polymerase can be G46E; G46E L329A; G46E E678G; G46E L329A E678G; G46E S671F; G46E D640G; G46E Q601R; G46E I669F; G46E D640G S671F; G46E L329A S671F; G46E L329A D640G; G46E L329A Q601R; G46E L329A I669F; G46E L329A D640G S671F; G46E S671F E678G; or G46E D640G E678G. In exemplary embodiments, these unmodified forms are substituted to provide a mutant polymerase with a T606S substitution. For example, the mutant chimeric DNA polymerase can be any one of the following: G46E T606S; G46E L329A T606S; G46E T606S E678G; G46E L329A T606S E678G; G46E T606S S671F; G46E T606S D640G; G46E Q601R T606S; G46E T606S I669F; G46E T606S D640G S671F; G46E L329A T606S S671F; G46E L329A T606S D640G; G46E L329A Q601R T606S; G46E L329A T606S I669F; G46E L329A T606S D640G S671F; G46E T606S S671F E678G; G46E T606S D640G E678G; or the like.

In various other aspects, the present invention provides a recombinant nucleic acid encoding a DNA polymerase as described herein, a vector comprising the recombinant nucleic acid, and a host cell transformed with the vector. In certain embodiments, the vector is an expression vector. Host cells comprising such expression vectors are useful in methods of the invention for producing the polymerase by culturing the host cells under conditions suitable for expression of the recombinant nucleic acid.

In yet another aspect, a method for conducting primer extension using a blocked primer is provided. The method generally includes contacting a DNA polymerase of the invention with a primer having a terminator nucleotide at the 3'-end, a polynucleotide template, pyrophosphate ($PP_i$) and free nucleotides under conditions suitable for removal of the terminator nucleotide, and extension of the primer, thereby producing an extended primer via pyrophosphorolysis activated polymerization (PAP). The free nucleotides can include unconventional nucleotides such as, e.g., ribonucleotides and/or labeled nucleotides. Further, the primer and/or template can include one or more nucleotide analogs. In some variations, the primer extension method is a method for polynucleotide amplification that includes contacting a DNA polymerase of the invention with a primer pair, the polynucleotide template, and the free nucleotides under conditions suitable for amplification of the polynucleotide.

The present invention also provides a kit useful in performing a PAP method. Generally, the kit includes at least one container providing a DNA polymerase of the invention as described herein. In certain embodiments, the kit further includes one or more additional containers providing one or more additional reagents. For example, in specific variations, the one or more additional containers provide free nucleotides; a buffer suitable for PAP; and/or a primer hybridizable, under PAP conditions, to a predetermined polynucleotide template. In some embodiments, the primer has a non-extendable terminator nucleotide at the 3'-terminal end.

BRIEF DESCRIPTION OF THE DRAWINGS

FIG. 1 depicts an amino acid sequence alignment of a region from the polymerase domain of exemplary thermostable DNA polymerases from various species of thermophilic bacteria and Bacteriophage T7: *Thermus thermophilus* (Tth) (SEQ ID NO:3), *Thermus caldophilus* (Tca) (SEQ ID NO:4), *Thermus* sp. Z05 (Z05) (SEQ ID NO:5), *Thermus aquaticus* (Taq) (SEQ ID NO:6), *Thermus flavus* (Tfl) (SEQ ID NO:7), *Thermus filiformis* (Tfi) (SEQ ID NO:8), *Thermus* sp. sps17 (Sps17) (SEQ ID NO:9), *Deinococcus radiodurans* (Dra) (SEQ ID NO:10), Hot Spring family B/clone 7 (HspB7) (SEQ ID NO:11), *Bacillus stearothermophilus* (Bst) (SEQ ID NO:12), *Bacillus caldotenax* (Bca) (SEQ ID NO:13), *Escherichia coli* (Eco) (SEQ ID NO:14), *Thermotoga maritima* (Tma) (SEQ ID NO:15), *Thermotoga neapolitana* (Tne) (SEQ ID NO:16), *Thermosipho africanus* (Taf) (SEQ ID NO:17), Hot Spring family A (HspA) (SEQ ID NO:18), chimeric thermostable DNA polymerase CS5 (SEQ ID NO:28), chimeric thermostable DNA polymerase CS6 (SEQ ID NO:29) and Bacteriophage T7 (T7) (SEQ ID NO:19). In addition, a sequence showing consensus amino acid residues among these exemplary sequences (SEQ ID NO:30) is also included. Note that the underlined residue in the consensus sequence is conserved in each of the bacterial species, as well as Bacteriophage T7, while the remaining residues in the consensus sequence (i.e. those not underlined) are conserved in the bacterial species, but not Bacteriophage T7. These motifs are highlighted in bold type for the CS5 polymerase sequence. The amino acid position amenable to mutation in accordance with the present invention is indicated with an asterisk (*).

FIG. 2A presents the amino acid sequence of the chimeric thermostable DNA polymerase CS5 (SEQ ID NO:20).

FIG. 2B presents a nucleic acid sequence encoding the chimeric thermostable DNA polymerase CS5 (SEQ ID NO:22).

FIG. 3A presents the amino acid sequence of the chimeric thermostable DNA polymerase CS6 (SEQ ID NO:21).

FIG. 3B presents a nucleic acid sequence encoding the chimeric thermostable DNA polymerase CS6 (SEQ ID NO:23).

DEFINITIONS

Figure 4:
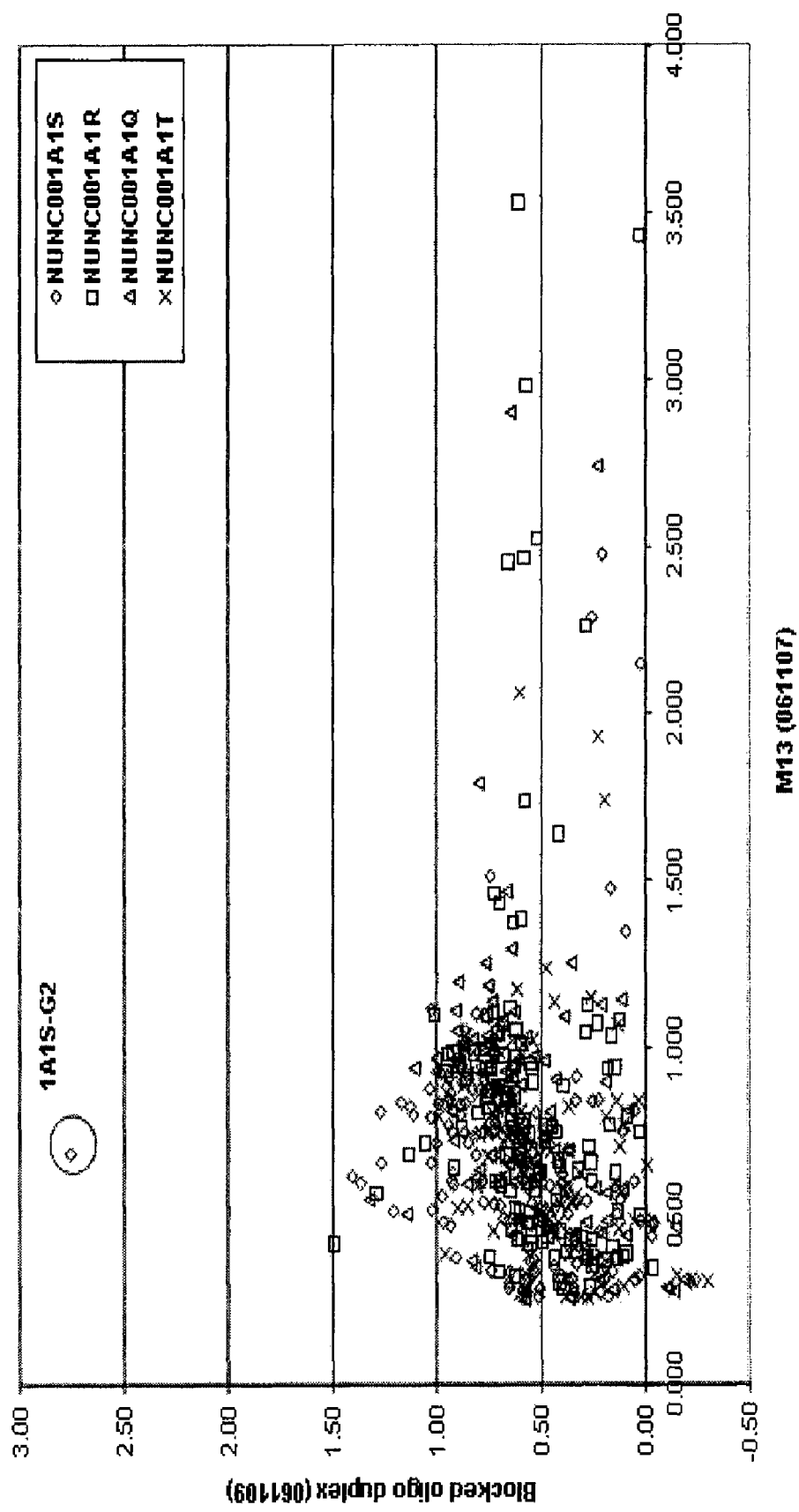
FIG. 4 shows the results of primer extension of an M13 template with a blocked oligo duplex.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "pyrophosphorolysis" as used herein refers to the removal of one or more nucleotides from the 3'-end of a nucleic acid in the presence of pyrophosphate ($PP_i$) to generate one or more nucleotide triphosphates.

The phrase "pyrophosphorolysis activated polymerization" or "PAP", as used herein refers to a method comprising a primer having a non-extendable terminator nucleotide at the 3'-end. In the presence of pyrophosphate (PPi), and hybridization of the blocked primer to a perfectly matched template, the DNA polymerases of the present invention will remove the non-extendable terminator nucleotide at the 3'-end of the primer. The polymerase will then extend the primer along the template from the newly created 3'-end following removal of the non-extendable terminator nucleotide. DNA polymerases of the present invention are deemed to have "improved PAP ability" if the rate of extension of a blocked primer with a modified or mutant polymerase of the invention is statistically faster than the rate of extension of a polymerase not having the mutation or modification, under the same reaction conditions. In some embodiments, a polymerase having improved PAP ability will have at least a 20% increase in the rate of extension of a blocked primer compared to a polymerase not having the mutation or modification. In some embodiments, the polymerases of the invention will show at least a 50% increase in the rate of extension of a blocked primer. In some embodiments, the polymerases of the invention will show at least a 100% increase, or more, in the rate of extension of a blocked primer compared to the same polymerase not having the modification or mutation under the same reaction conditions.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry*, 5<sup>th</sup> ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," *Proc. Natl. Acad. Sci. U.S.A.* 101 (24):8882-8887, Anderson et al. (2004) "An expanded genetic code with a functional quadruplet codon" *Proc. Natl. Acad. Sci. U.S.A.* 101(20):7566-7571, Ikeda et al. (2003) "Synthesis of a novel histidine analogue and its efficient incorporation into a protein in vivo," *Protein Eng. Des. Sel.* 16(9):699-706, Chin et al. (2003) "An Expanded Eukaryotic Genetic Code," *Science* 301(5635):964-967, James et al (2001) "Kinetic characterization of ribonuclease S mutants containing photoisomerizable phenylazophenylalanine residues," *Protein Eng. Des. Sel.* 14(12):983-991, Kohrer et al. (2001) "Import of amber and ochre suppressor tRNAs into mammalian cells: A general approach to site-specific insertion of amino acid analogues into proteins," *Proc. Natl. Acad. Sci. U.S.A.* 98(25):14310-14315, Bacher et al. (2001) "Selection and Characterization of *Escherichia coli* Variants Capable of Growth on an Otherwise Toxic Tryptophan Analogue," *J. Bacteriol.* 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," *J. Biol. Chem.* 275(51):40324-40328, and Budisa et al. (2001) "Proteins with β-(thienopyrrolyl)alanines as alternative chromophores and pharmaceutically active amino acids," *Protein Sci.* 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "mutant" in the context of DNA polymerases of the present invention, means a polypeptide, typically recombinant, that has been altered to include one or more amino acid substitutions, additions, or deletions relative to a corresponding unmodified form of the DNA polymerase.

The term "modified form" or "modified mutant" in the context of a DNA polymerase of the invention refers to a functional DNA polymerase in which at least the residue at position $X_6$ in SEQ ID NO:24 is not T or $X_{10}$ in SEQ ID NO:25 is not T or A, and where the polymerase exhibits improved PAP ability compared to an unmodified form of the polymerase.

The term "unmodified form," or "unmodified mutant" in the context of a DNA polymerase of the instant invention refers to a functional DNA polymerase wherein the amino acid residue at position $X_6$ in SEQ ID NO:24 is T or position $X_{10}$ in SEQ ID NO:25 is T or A. The unmodified form of a DNA polymerase of the invention can be, for example, a wild-type and/or a naturally occurring DNA polymerase. An unmodified form of a DNA polymerase can also be a mutant protein that has been intentionally mutated at a position other than $X_6$ in SEQ ID NO:24 or $X_{10}$ in SEQ ID NO:25 to provide desired functionality, e.g., improved incorporation of dideoxyribonucleotides, ribonucleotides, ribonucleotide analogs, dye-labeled nucleotides, modulating 5'-nuclease activity, modulating 3'-nuclease (or proofreading) activity, or the like. An unmodified form of the polymerase is preferably a thermostable DNA polymerase, such as DNA polymerases from various thermophilic bacteria, as well as functional variants thereof having substantial sequence identity to a wild-type or naturally occurring thermostable polymerase. Such variants can include, for example, chimeric DNA polymerases such as, for example, the chimeric DNA polymerases described in U.S. Pat. No. 6,228,628 and U.S. Application Publication No. 2004/0005599, which are incorporated by reference herein in their entirety. In certain embodiments, the unmodified form of a polymerase has pyrophosphorolysis activated polymerization (PAP) ability.

The term "thermostable polymerase," refers to an enzyme that is stable to heat, is heat resistant, and retains sufficient activity to effect subsequent primer extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). "Irreversible denaturation" for purposes herein refers to permanent and complete loss of enzymatic activity. For a thermostable polymerase, "enzymatic activity" refers to the catalysis of the combination of the nucleotides in the proper manner to form primer extension products that are complementary to a template nucleic acid strand. Non-limiting exemplary thermostable DNA polymerases from thermophilic bacteria include, e.g., DNA polymerases from *Thermotoga maritima, Thermus aquaticus, Thermus thermophilus, Thermus flavus, Thermus filiformis, Thermus* species sps17, *Thermus* species Z05, *Thermus caldophilus, Bacillus caldotenax, Thermotoga neopolitana*, and *Thermosipho africanus*.

As used herein, a "chimeric" protein refers to a protein whose amino acid sequence represents a fusion product of subsequences of the amino acid sequences from at least two distinct proteins. A chimeric protein typically is not produced by direct manipulation of amino acid sequences, but, rather, is expressed from a "chimeric" gene that encodes the chimeric amino acid sequence. In certain embodiments, for example, an unmodified form of a mutant DNA polymerase of the present invention is a chimeric protein that consists of an amino-terminal (N-terminal) region derived from a *Thermus* species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus.

In the context of mutant DNA polymerases, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified DNA polymerase represents referral to a collection of equivalent positions in other recognized DNA polymerases and structural homologues and families. In typical embodiments of the present invention, "correspondence" of amino acid positions are determined with respect to a region of the polymerase comprising the motif of a consensus sequence (e.g. SEQ ID NO:1), as discussed further herein.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above. A recombinant protein is typically distinguished from naturally occurring protein by at least one or more characteristics.

The term "nucleic acid" refers to nucleotides (e.g., ribonucleotides, deoxyribonucleotides, 2'-terminator nucleotides, dideoxynucleotides, etc.) and polymers (e.g., comprising deoxyribonucleic acids (DNAs), ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), PNA-DNA conjugates, PNA-RNA conjugates, etc.) that comprise such nucleotides covalently linked together, either in a linear or branched fashion.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321), O-methylphosphoroamidite linkages (see Eckstein, *Oligonucleotides and Analogues: A Practical Approach*, Oxford University Press (1992)), and peptide nucleic acid backbones and linkages (see, Egholm (1992) *J. Am. Chem. Soc.* 114:1895; Meier et al. (1992) *Chem. Int. Ed. Engl.* 31:1008; Nielsen (1993) *Nature* 365:566; Carlsson et al. (1996) *Nature* 380:207), which references are each incorporated by reference. Other analog nucleic acids include those with positively charged backbones (Denpcy et al. (1995) *Proc. Natl. Acad. Sci. USA* 92: 6097); non-ionic backbones (U.S. Pat. Nos. 5,386,023, 5,637, 684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook. Nucleic acids containing one or more carbocyclic sugars are also included within the definition of nucleic acids (see Jenkins et al. (1995) *Chem. Soc. Rev.* pp 169-176). Several nucleic acid analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 1, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.).

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

An "oligonucleotide" refers to a nucleic acid that includes at least two nucleotides, typically more than three nucleotides, and more typically greater than ten nucleotides. The exact size of an oligonucleotide generally depends on various factors, including the ultimate function or use of the oligonucleotide. Oligonucleotides are optionally prepared by any suitable method, including, for example, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103: 3185-3191; automated synthesis methods; or the solid support method of U.S. Pat. No. 4,458,066, among other methods known in the art, which references are each incorporated by reference.

A "primer nucleic acid" is typically a nucleic acid that can hybridize to a template nucleic acid and permit chain extension or elongation using, e.g., a nucleotide incorporating biocatalyst, such as a thermostable polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. A primer nucleic acid can be labeled, if desired, by incorporating a label detectable by, e.g., spectroscopic, photochemical, biochemical, immunochemical, or chemical techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. In addition, a primer nucleic acid can simply provide a substrate for a nucleotide incorporating biocatalyst in a template independent manner.

An "extended primer nucleic acid" refers to a primer nucleic acid to which one or more additional nucleotides have been added or otherwise incorporated (e.g., covalently bonded to).

A "template nucleic acid" refers to a nucleic acid to which a primer nucleic acid can hybridize and be extended. Accordingly, template nucleic acids include subsequences that are at least partially complementary to the primer nucleic acids. Template nucleic acids can be derived from essentially any source. To illustrate, template nucleic acids are optionally derived or isolated from, e.g., cultured microorganisms, uncultured microorganisms, complex biological mixtures, tissues, sera, pooled sera or tissues, multispecies consortia, ancient, fossilized or other nonliving biological remains, environmental isolates, soils, groundwaters, waste facilities, deep-sea environments, or the like. Further, template nucleic acids optionally include or are derived from, e.g., individual cDNA molecules, cloned sets of cDNAs, cDNA libraries, extracted RNAs, natural RNAs, in vitro transcribed RNAs, characterized or uncharacterized genomic DNAs, cloned genomic DNAs, genomic DNA libraries, enzymatically fragmented DNAs or RNAs, chemically fragmented DNAs or RNAs, physically fragmented DNAs or RNAs, or the like. Template nucleic acids can also be chemically synthesized using techniques known in the art. In addition, template nucleic acids optionally correspond to at least a portion of a gene or are complementary thereto. As used herein, a "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extendible nucleotide" refers to a nucleotide to which at least one other nucleotide can be added or covalently bonded, e.g., in a reaction catalyzed by a nucleotide incorporating biocatalyst once the extendible nucleotide is incorporated into a nucleotide polymer. Examples of extendible nucleotides include deoxyribonucleotides and ribonucleotides. An extendible nucleotide is typically extended by adding another nucleotide at a 3'-position of the sugar moiety of the extendible nucleotide.

A "non-extendible" nucleotide refers to a nucleotide, which upon incorporation into a nucleic acid prevents further extension of the nucleic acid, e.g., by at least one nucleotide incorporating biocatalyst. An exemplary non-extendable nucleotide suitable for use with the invention are 2'-terminator nucleotides.

A "2'-terminator nucleotide" refers to a nucleotide analog that comprises a blocking group (BG) at the 2'-position of the sugar moiety of the nucleotide. A "blocking group" refers to a chemical group or moiety that typically prevents the extension of a nucleic acid (i.e., a 2'-terminator nucleotide is typically non-extendible by one or more nucleotide incorporating biocatalysts). That is, once a 2'-terminator nucleotide is incorporated into a nucleic acid (e.g., at a 3'-terminal end of the nucleic acid), the blocking group prevents further extension of a nucleic acid by at least one nucleotide incorporating biocatalyst selected from, e.g., a G46E E678G CS5 polymerase, a G46E E678G CS6 polymerase, a ΔZ05R polymerase, an E615G Taq DNA polymerase, a TFL *Thermus flavus* polymerase, a TMA-25 polymerase, a TMA-30 polymerase, a Tth DNA polymerase, a *Thermus* SPS-17 polymerase, an E615G Taq polymerase, a *Thermus* Z05R polymerase, a T7 DNA polymerase, a Komberg DNA polymerase I, a Klenow DNA polymerase, a Taq DNA polymerase, a Micrococcal DNA polymerase, an alpha DNA polymerase, a reverse transcriptase, an AMV reverse transcriptase, a M-MuLV reverse transcriptase, a DNA polymerase, an RNA polymerase, an *E. coli* RNA polymerase, a SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and/or the like. An exemplary blocking group is a phosphate group. Other representative blocking groups are also described herein. Exemplary 2'-terminator nucleotides include 2'-monophosphate-3'-hydroxyl-5'-triphosphate nucleosides and 2'-monophosphate-3'-hydroxyl-5'-diphosphate nucleosides. Other 2'-terminator nucleotides are also described further herein and in, e.g., U.S. Pat. Pub. Nos. 20070154914, 20050037991, and 20050037398.

A "moiety" or "group" refers to one of the portions into which something, such as a molecule, is divided (e.g., a functional group, substituent group, or the like). For example, a nucleotide typically comprises a basic group (e.g., adenine, thymine, cytosine, guanine, uracil, or an analog basic group), a sugar moiety (e.g., a moiety comprising a sugar ring or an analog thereof), and one or more phosphate groups.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleic acid extension rate" refers the rate at which a biocatalyst (e.g., an enzyme, such as a polymerase, ligase, or the like) extends a nucleic acid (e.g., a primer or other oligonucleotide) in a template-dependent or template-independent manner by attaching (e.g., covalently) one or more nucleotides to the nucleic acid. To illustrate, certain mutant DNA polymerases described herein have improved nucleic acid extension rates relative to unmodified forms of these DNA polymerases, such that they can extend primers at higher rates than these unmodified forms under a given set of reaction conditions.

A "mixture" refers to a combination of two or more different components. A "reaction mixture" refers a mixture that comprises molecules that can participate in and/or facilitate a given reaction. For example, a "DNA sequencing reaction mixture" refers to a reaction mixture that comprises components necessary for a DNA sequencing reaction. Thus, a DNA sequencing reaction mixture is suitable for use in a DNA sequencing method for determining the nucleic acid sequence of a template or target nucleic acid, although the reaction mixture may initially be incomplete, so that the initiation of the sequencing reaction is controlled by the user. In this manner, the reaction may be initiated once a final component, such as the enzyme, is added, to provide a complete DNA sequencing reaction mixture. Typically, a DNA sequencing reaction will contain a buffer, suitable for polymerization activity, extendible nucleotides, and at least one 2'-terminator nucleotide. The reaction mixture also may contain a primer nucleic acid suitable for extension on a template nucleic acid by a polymerase enzyme. Either the primer nucleic acid or one of the nucleotides is generally labeled with a detectable moiety such as a fluorescent label. Generally, the reaction is a mixture that comprises four extendible nucleotides and at least one 2'-terminator nucleotide. Typically, the polymerase is a thermostable DNA polymerase (e.g., a G46E E678G CS5 DNA polymerase, a G46E E678G CS6 DNA polymerase, an E615G Taq DNA polymerase, a ΔZ05R DNA polymerase, a G46E L329A E678G CS5 DNA polymerase, etc.) and the 2'-terminator nucleotide is a 2'-monophosphate-3'-hydroxyl-5'-triphosphate nucleoside.

DETAILED DESCRIPTION OF THE INVENTION

I. Introduction

The present invention provides for novel DNA polymerases having improved pyrophosphorolysis activated polymerization (PAP) ability. The DNA polymerases of the invention have the ability to rapidly activate and extend primers that end in an extension terminator nucleotide that must be removed by pyrophosphorolysis before the primer can be extended. Typically, several parameters must be optimized for each primer pair used in a PAP reaction. Common parameters that are typically optimized include polymerase concentration, $PP_i$ concentration, extension time and temperature. The novel DNA polymerases of the present invention can rapidly activate a wide variety of blocked primers when bound to a perfectly matched template without the optimization procedures required with currently available polymerases. The DNA polymerases are therefore useful in a variety of applications involving primer extension or amplification of polynucleotide templates, including for example, applications in recombinant DNA studies and medical diagnosis of disease involving rare allele detection.

In practicing aspects of the present invention (e.g., producing modified enzymes, performing amplification reactions, etc.), many conventional techniques in molecular biology and recombinant DNA are optionally utilized. These techniques are well known and are explained in, for example, *Current Protocols in Molecular Biology, Volumes I, II, and III,* 1997 (F. M. Ausubel ed.); Sambrook et al., 2001, *Molecular Cloning: A Laboratory Manual,* Third Edition, Cold Spring Harbor Laboratory Press, Cold Spring Harbor, N.Y.; Berger and Kimmel, *Guide to Molecular Cloning Techniques, Methods in Enzymology* volume 152 Academic Press, Inc., San Diego, Calif. (Berger), *DNA Cloning: A Practical Approach, Volumes I and II,* 1985 (D. N. Glover ed.); *Oligonucleotide Synthesis,* 1984 (M. L. Gait ed.); *Nucleic Acid Hybridization,* 1985, (Hames and Higgins); *Transcription and Translation,* 1984 (Hames and Higgins eds.); *Animal Cell Culture,* 1986 (R. I. Freshney ed.); *Immobilized Cells and Enzymes,* 1986 (IRL Press); Perbal, 1984, *A Practical Guide to Molecular Cloning*; the series, *Methods in Enzymology* (Academic Press, Inc.); *Gene Transfer Vectors for Mammalian Cells,* 1987 (J. H. Miller and M. P. Calos eds., Cold Spring Harbor Laboratory); and *Methods in Enzymology* Vol. 154 and Vol. 155 (Wu and Grossman, and Wu, eds., respectively).

II. Modified DNA Polymerases Having Improved Pap Ability

In some embodiments, the DNA polymerases of the invention comprise the following amino acid motif:

Arg-Xaa-Xaa-Xaa-Lys-Leu-Xaa-Xaa-Xaa*-Tyr-Xaa-Xaa-Xaa-Xaa-Xaa (also referred to herein in the one-letter code as R-$X_1$-$X_2$-$X_3$-K-L-$X_4$-$X_5$-$X_6$*-Y-$X_7$-$X_8$-$X_9$-$X_{10}$-$X_{11}$) (SEQ ID NO:1), wherein $X_6$ is not T and the polymerase has improved nucleic acid extension rate of a blocked primer relative to an otherwise identical DNA polymerase where $X_6$ is T.

In some embodiments, $X_1$-$X_5$, and $X_7$-$X_{11}$ are any amino acid.

In some embodiments,
$X_2$ is Leu (L), Ile (I), Tyr (Y)
$X_4$ is Lys (K), Arg (R), Gln (Q)
$X_5$ is Asn (N), Ser (S), Gly (G)
$X_6$ is any amino acid except Thr (T)
$X_8$ is Asp (D) or Glu (E)
$X_{10}$ is Leu (L) or Ile (I)
$X_{11}$ is Pro (P) or Leu (L) (SEQ ID NO:36).

In some embodiments, the amino acid at position $X_6$ is selected from the group consisting of (G), (A), (L), (M), (F), (W), (K), (Q), (E), (S), (P), (V), (I), (C), (Y), (H), (R), (N), and (D) (SEQ ID NO:38). In some embodiments, $X_6$ is S (SEQ ID NO:39).

In some embodiments of SEQ ID NO:1, $X_1$-$X_5$, and $X_7$-$X_{11}$ are any amino acids found in corresponding positions in any DNA polymerase. Non-limiting exemplary DNA polymerases include *Thermus thermophilus, Thermus caldophilus, Thermus* sp. Z05, *Thermus aquaticus, Thermus flavus, Thermus filiformis, Thermus* sp. sps17, *Deinococcus radiodurans,* Hot Spring family B/clone 7, *Bacillus stearothermophilus, Bacillus caldotenax, Escheria coli, Thermotoga maritima, Thermotoga neapolitana, Thermosipho africanus,* and Hot Spring family A. In some embodiments, $X_1$ is selected from the group consisting of Glu (E), Gln (Q), Gly (G), Lys (K), and Thr (T) (SEQ ID NO:52). In some embodiments, $X_3$ is selected from the group consisting of Thr (T), Met (M), Asp (D), Ser (S), Gly (G), Ala (A), Gln (Q), and Leu (L) (SEQ ID NO:53). In some embodiments, $X_7$ is selected from the group consisting of Val (V), Ile (I), Leu (L), Ala (A), Thr (T) (SEQ ID NO:54). In some embodiments, $X_9$ is selected from the group consisting of Pro (P), Ala (A), Gly (G), Lys (K), Thr (T), Ser (S) (SEQ ID NO:55).

In other embodiments, the DNA polymerases of the invention comprise the following amino acid motif:

Xaa-Xaa-Xaa-Xaa-Lys-Xaa-Xaa-Xaa-Xaa-Xaa-Xaa-Xaa-Xaa-Xaa-Xaa-Xaa-Xaa (also referred to herein in the one letter code as $X_1$-$X_2$-$X_3$-$X_4$-K-$X_5$-$X_6$-$X_7$-$X_8$-$X_9$-$X_{10}$-$X_{11}$-$X_{12}$-$X_{13}$-$X_{14}$-$X_{15}$-$X_{16}$; (SEQ ID NO:2) wherein $X_{10}$ is not T or A and the polymerase has an improved nucleic acid extension rate of a blocked primer relative to an otherwise identical DNA polymerase where $X_{10}$ is T or A. In some embodiments, $X_1$-$X_9$ and $X_{11}$-$X_{16}$ are any amino acid. In some embodiments,
$X_1$ is R or L
$X_3$ is L, I, or Y
$X_5$ is R or L
$X_6$ is I or absent
$X_7$ is G or absent
$X_8$ is K, R, or Q
$X_9$ is N, S, or G
$X_{10}$ is T or A
$X_{11}$ is Y or E
$X_{13}$ is D or E
$X_{15}$ is L, I, or A
$X_{16}$ is P, L, or W (SEQ ID NO:40).

In some embodiments, the amino acid at position $X_{10}$ is selected from the group consisting of (G), (L), (M), (F), (W), (K), (Q), (E), (S), (P), (V), (I), (C), (Y), (H), (R), (N), and (D) (SEQ ID NO:42). In some embodiments, $X_{10}$ is S (SEQ ID NO:43).

In some embodiments of SEQ ID NO:2, $X_2$, $X_4$, $X_{12}$, and $X_{14}$ are any amino acids as found in corresponding positions in any DNA polymerase, e.g. DNA polymerases from *Thermus thermophilus*, *Thermus caldophilus*, *Thermus* sp. Z05, *Thermus aquaticus*, *Thermus flavus*, *Thermus filiformis*, *Thermus* sp. sps17, *Deinococcus radiodurans*, Hot Spring family B/clone 7, *Bacillus stearothermophilus*, *Bacillus caldotenax*, *Escheria coli*, *Thermotoga maritima*, *Thermotoga neapolitana*, *Thermosipho africanus*, Hot Spring family A, and Bacteriophage T7. In some embodiments, $X_2$ is selected from the group consisting of Glu (E), Gln (Q), Gly (G), Lys (K), Thr (T), and Met (M) (SEQ ID NO:56). In some embodiments, $X_4$ is selected from the group consisting of Thr (T), Met (M), Asp (D), Ser (S), Gly (G), Ala (A), Gln (Q), and Leu (L) (SEQ ID NO:57). In some embodiments, $X_{12}$ is selected from the group consisting of Val (V), Ile (I), Leu (L), Ala (A), Thr (T), and Gly (G) (SEQ ID NO:58). In some embodiments, $X_{14}$ is selected from the group consisting of Pro (P), Ala (A), Gly (G), Lys (K), Thr (T), and Ser (S) (SEQ ID NO:59).

An unmodified form of DNA polymerases amenable to mutation in accordance with the present invention (as shown in e.g., SEQ ID NO:24) are those having a functional polymerase domain comprising the following amino acid motif:

R-$X_1$-$X_2$-$X_3$-K-L-$X_4$-$X_5$-$X_6$-Y-$X_7$-$X_8$-$X_9$-$X_{10}$-$X_{11}$ (SEQ ID NO:24) wherein $X_6$ is T In some embodiments, $X_1$-$X_5$, and $X_7$-$X_{11}$ are any amino acid.

In some embodiments,
$X_2$ is L, I, or Y
$X_4$ is K, R, or Q
$X_5$ is N, S, or G
$X_6$ is T
$X_8$ is D or E
$X_{10}$ is L or I
$X_{11}$ is P or L (SEQ ID NO:44).

In some embodiments, the unmodified form of DNA polymerases amenable to mutation in accordance with the present invention (as shown in e.g., SEQ ID NO:25) are those having a functional polymerase domain comprising the following amino acid motif:

$X_1$-$X_2$-$X_3$-$X_4$-K-$X_5$-$X_6$-$X_7$-$X_8$-$X_9$-$X_{10}$-$X_{11}$-$X_{12}$-$X_{13}$-$X_{14}$-$X_{15}$-$X_{16}$, wherein $X_{10}$ is T or A.

In some embodiments, $X_1$-$X_9$, and $X_{11}$-$X_{16}$ are any amino acid.

In some embodiments,
$X_1$ is R or L
$X_3$ is L, I, or Y
$X_5$ is R or L
$X_6$ is I or absent
$X_7$ is G or absent
$X_8$ is K, R, or Q
$X_9$ is N, S, or G
$X_{10}$ is T or A
$X_{11}$ is Y or E
$X_{13}$ is D or E
$X_{15}$ is L, I, or A
$X_{16}$ is P, L, or W (SEQ ID NO:48).

The motifs presented above (e.g., SEQ ID NO:24 and SEQ ID NO:25) are present within the 3/A subdomain of many family A type DNA-dependent DNA polymerases, particularly thermostable DNA polymerases from thermophilic bacteria (SEQ ID NO:24) and Bacteriophage T7 (SEQ ID NO:25). For example, FIG. 1 shows an amino acid sequence alignment of a region from the 3/A subdomain from several species of bacteria: *Thermus thermophilus*, *Thermus caldophilus*, *Thermus* sp. Z05, *Thermus aquaticus*, *Thermus flavus*, *Thermus filiformis*, *Thermus* sp. sps17, *Deinococcus radiodurans*, Hot Spring family B/clone 7, *Bacillus stearothermophilus*, *Bacillus caldotenax*, *Escheria coli*, *Thermotoga maritima*, *Thermotoga neapolitana*, *Thermosipho africanus*, Hot Spring family A, and Bacteriophage T7. The amino acid sequence alignment shown in FIG. 1 also includes representative chimeric thermostable DNA polymerases. As shown, the motif in SEQ ID NO:24 and SEQ ID NO:25 are present in each of these polymerases indicating a conserved function for this region of the polymerase.

Accordingly, in some embodiments, the unmodified form of the DNA polymerase is a wild-type or a naturally occurring DNA polymerase, such as, for example, a polymerase selected from any of the species of bacteria listed above. In some embodiments of the invention, the polymerase is from a species of the genus *Thermus*. In other embodiments of the invention, the unmodified polymerase is from a thermophilic species other than *Thermus*. The full nucleic acid and amino acid sequence for numerous thermostable DNA polymerases are readily available and known to persons of skill in the art. For example, the sequences each of *Thermus aquaticus* (Taq), *Thermus thermophilus* (Tth), *Thermus* species Z05, *Thermus* species sps17, *Thermotoga maritima* (Tma), and *Thermosipho africanus* (Taf) polymerase have been published in PCT Intl. Pat. Pub. No. WO 92/06200. The sequence for the DNA polymerase from *Thermus flavus* has been published in Akhmetzjanov and Vakhitov (*Nucleic Acids Research* 20:5839, 1992). The sequence of the thermostable DNA polymerase from *Thermus caldophilus* is found in EMBL/GenBank Accession No. U62584. The sequence of the thermostable DNA polymerase from *Thermus filiformis* can be recovered from ATCC Deposit No. 42380 using, e.g., the methods provided in U.S. Pat. No. 4,889,818, as well as the sequence information provided therein. The sequence of the *Thermotoga neapolitana* DNA polymerase is from GeneSeq Patent Data Base Accession No. R98144 and PCT WO 97/09451. The sequence of the thermostable DNA polymerase from *Bacillus* caldotenax is described in, e.g., Uemori et al. (*J Biochem (Tokyo)* 113(3):401-410, 1993; (see also, Swiss-Prot database Accession No. Q04957 and GenBank Accession Nos. D12982 and BAA02361). The sequence for the DNA polymerase from *Bacillus stearothermophilus* has been published in U.S. Pat. No. 6,066,483. Examples of unmodified forms of DNA polymerases that can be modified as described herein are also described in, e.g., U.S. Pat. Nos. 6,228,628; 6,346,379; 7,030,220; 6,881,559; 6,794,177; 6,468,775; and U.S. Pat. Appl. Nos. 20040005599; 20020012970; 20060078928; 20040115639.

In some embodiments, the unmodified form of a polymerase is a functional DNA polymerase that has been previously mutated (e.g., by amino acid substitution, addition, or deletion), provided that the previously mutated polymerase retains the amino acid motif of SEQ ID NOS:24 or 25. Thus, suitable unmodified DNA polymerases also include functional variants of wild-type or naturally occurring polymerases. Such variants typically will have substantial sequence identity or similarity to the wild-type or naturally occurring polymerase, typically at least 80% sequence identity and more typically at least 90%, 95%, or 98% sequence identity. In certain embodiments, the unmodified DNA polymerase has pyrophosphorolysis activated polymerization ability (PAP).

Suitable polymerases also include, for example, certain chimeric DNA polymerases comprising polypeptide regions from two or more enzymes. Examples of such chimeric DNA polymerases are described in, e.g., U.S. Pat. No. 6,228,628, which is incorporated by reference herein in its entirety. Particularly suitable are chimeric CS-family DNA polymerases, which include the CS5 (SEQ ID NO:20) and CS6 (SEQ ID NO:21) polymerases and variants thereof having substantial sequence identity or similarity to SEQ ID NO:20 or SEQ ID NO:21 (typically at least 80% sequence identity and more typically at least 90% sequence identity). The CS5 and CS6 DNA polymerases are chimeric enzymes derived from *Thermus* sp. Z05 and *Thermotoga maritima* (Tma) DNA polymerases. They comprise the N-terminal 5'-nuclease domain of the *Thermus* enzyme and the C-terminal 3'-5' exonuclease and the polymerase domains of the Tma enzyme. These enzymes have efficient reverse transcriptase activity, can extend nucleotide analog-containing primers, and can incorporate alpha-phosphorothioate dNTPs, dUTP, dITP, and also fluorescein- and cyanine-dye family labeled dNTPs. The CS5 and CS6 polymerases are also efficient $Mg^{2+}$-activated PCR enzymes. Nucleic acid sequences encoding CS5 and CS6 polymerases are provided in FIGS. 2B and 3B, respectively. CS5 and CS6 chimeric polymerases are further described in, e.g., U.S. Pat. Pub. No. 20040005599.

In some embodiments, the unmodified form of the DNA polymerase is a polymerase that has been previously mutated, typically by recombinant means, to confer some selective advantage. Such modifications include, for example, the amino acid substitutions G46E, L329A, and/or E678G in the CS5 DNA polymerase, CS6 DNA polymerase, or corresponding mutation(s) in other polymerases. Accordingly, in some embodiments, the unmodified form of the DNA polymerase is one of the following (each having the amino acid sequence of SEQ ID NO:20 or SEQ ID NO:21 except for the designated substitution(s)): G46E; G46E L329A; G46E E678G; or G46E L329A E678G. The E678G substitution, for example, allows for the incorporation of ribonucleotides and other 2'-modified nucleotides, but this mutation also appears to result in an impaired ability to extend primed templates. In certain embodiments, the mutations according to the present invention, which result in a faster extension rate of the mutant polymerase, ameliorate the E678G mutation's impaired ability to extend primed templates.

The modified form of DNA polymerases of the present invention comprise one or more amino acid substitutions relative to the unmodified form of the polymerase, i.e. at position $X_6$ of SEQ ID NO:24 or $X_{10}$ of SEQ ID NO:25. Amino acid substitution at this position confers improved PAP ability yielding a DNA polymerase with an improved (e.g., faster) nucleic acid extension rate relative to the corresponding DNA polymerase that is otherwise identical but includes a T at position $X_6$ of SEQ ID NO:24, or a T or A at position $X_{10}$ of SEQ ID NO:25.

Because the unmodified forms of DNA polymerase are unique, the amino acid position corresponding to $X_6$ of SEQ ID NO:24 or $X_{10}$ of SEQ ID NO:25 is typically distinct for each mutant polymerase. Amino acid and nucleic acid sequence alignment programs are readily available (see, e.g., those referred to supra) and, given the particular motif identified herein, serve to assist in the identification of the exact amino acids (and corresponding codons) for modification in accordance with the present invention. The positions corresponding to $X_6$ of SEQ ID NO:24 or $X_{10}$ of SEQ ID NO:25 are shown in Table 1 for representative chimeric thermostable DNA polymerases and thermostable DNA polymerases from exemplary thermophilic species.

TABLE 1

Amino Acid Positions Corresponding to Motif Position $X_6$ of SEQ ID NO: 1 or 24 or $X_{10}$ in SEQ ID NO: 2 or 25 in Exemplary Thermostable Polymerases.

| Organism or Chimeric Sequence Consensus | Position $X_6$ (SEQ ID NOS: 1 and 24) or $X_{10}$ (SEQ ID NOS: 2 and 25) |
|---|---|
| *T. thermophilus* | 546 |
| *T. caldophilus* | 546 |
| T. sp. Z05 | 546 |
| *T. aquaticus* | 544 |
| *T. flavus* | 543 |
| *T. filiformis* | 542 |
| T. sp. Sps17 | 542 |
| *D. radiodurans* | 634 |
| Hot Spring family B/clone 7 | 592 |
| *B. stearothermophilus* | 586 |
| *B. caldotenax* | 587 |
| *E. coli* | 639 |
| *T. maritime* | 606 |
| *T. neapolitana* | 606 |
| *T. africanus* | 605 |
| Hot Spring family A | 643 |
| CS5 | 606 |
| Bacteriophage T7 | 400 |

As previously discussed, in some embodiments, the mutant DNA polymerase of the present invention is derived from CS5 DNA polymerase (SEQ ID NO:20), CS6 DNA polymerase (SEQ ID NO:21), or a variant of those polymerases (e.g., G46E; G46E L329A; G46E E678G; G46E L329A E678G; and the like). As referred to above, in CS5 DNA polymerase, mutatable position $X_6$ corresponds to Thr (T) at position 606. Thus, in certain variations of the invention, the modified form of the polymerase comprises an amino acid substitution at position $X_6$, relative to a CS5 DNA polymerase or a CS6 DNA polymerase that is otherwise identical. Exemplary modified CS5 DNA polymerase and CS6 DNA polymerase mutants include those comprising the amino acid substitution T606S. Other, exemplary modified CS5 DNA and CS6 DNA polymerase mutants include the following (each having the amino acid sequence of SEQ ID NO:20 or SEQ ID NO:21 except for the designated substitutions):

G46E T606S;
G46E L329A T606S;
G46E T606S E678G;
L329A T606S E678G;
G46E L329A T606S E678G;
G46E T606S S671F;
G46E T606S D640G;
G46E Q601R T606S;
G46E T606S I669F;
G46E T606S D640G S671F;
G46E L329A T606S S671F;
G46E L329A T606S D640G;
G46E L329A Q601R T606S;
G46E L329A T606S I669F;
G46E L329A T606S D640G S671F;
G46E T606S S671F E678G;
G46E T606S D640G E678G; and the like.

A. Method for Determining Relative Rate of Extension of a Blocked Primer

In order to determine whether a modified (or mutant) DNA polymerase of the invention has an improved rate of activation of 2'-$PO_4$-blocked primers, an extension assay is performed. In some embodiments of the extension assay, a pre-annealed oligo duplex substrate is substituted for a primed M13 template. In some embodiments, the primer strand has the sequence: CGCCTGGTCTGTACACCGTTCE (SEQ ID NO:34), where E=2'PO$_4$-dA, and the template strand has the sequence: CAACTTTGAAAGAGGACAGATGAACG-GTQTACAQACCAQGCGP (SEQ ID NO:35), where Q=7-deaza-dG, and P=3' PO$_4$. The 7-deaza-dG residues in the template strand results in reduced background fluorescence. In some embodiments, the oligo duplex is added to the reaction mix (0.5 mM pyrophosphate, 100 mM Tricine pH 8.0, 20 mM KOAc, 3 mM Mg(OAc)$_2$, 2.5% Enzyme Storage Buffer, 1×SYBR Green I (Molecular Probes), and 0.1 mM each dATP, dCTP, dGTP, and dTTP. ("Enzyme Storage Buffer" is composed of 20 mM Tris pH 8.0, 100 mM KCl, 0.1 mM EDTA, 1 mM DTT, 0.5% Tween 20, and 50% v/v glycerol.) at 100 nM. The rate at which the DNA polymerases are able to activate the blocked primer is estimated by the rate of change in fluorescence, after background subtraction. In order to distinguish extension-derived fluorescence from background fluorescence, parallel reactions can be included in which primer strand extension is prevented by leaving out the nucleotides from the reaction master mix. For each polymerase of the invention, activity can be estimated from the rate of increase in fluorescence, after background subtraction, and then compared to the activity on an M13 template. The ratio of these two rates (for each polymerase) is then used to determine which modified (or mutant) DNA polymerases have relatively high 2'-PO$_4$-blocked primer activation activity. This assay is described in more detail in Example 1.

In order to determine if a modified DNA polymerase of the invention wherein $X_6$ is not T (SEQ ID NO:1) or $X_{10}$ is not T or A (SEQ ID NO:2) has an improved ability to extend a blocked primer relative to an otherwise identical DNA polymerase wherein $X_6$ is T (SEQ ID NO:24) or $X_{10}$ is T or A (SEQ ID NO:25) PAP-PCR is performed with a model system that utilizes M13 mp18 as the template. The primers for use with the model system have the sequences:

```
KAB77:   CGCCTGGTCTGTACACCGTTCE,   (SEQ ID NO:26)
where E = 2'PO4-dA,
and

KAB71:   GGAACGAGGGTAGCAACGGCTACE, (SEQ ID NO:27)
where E = 2'PO4-dA.
```

Together the two primers are expected to make a 342 bp amplicon from M13 template. Note that both primers are blocked with a 2'-PO$_4$ group at the 3'-end, and cannot be extended until that group is removed by pyrophosphorolysis of the terminal dA residue. Previous observations have indicated that the rate of activation by pyrophosphorolysis of different 2'-PO$_4$-blocked primers varies, and that KAB77 activation is relatively slow, requiring long extension times of up to 5 minutes in the PCR to achieve efficient amplification.

The reaction conditions used to test the polymerases are: 50 mM Tricine (pH 7.5), 80 mM KOAc (pH 7.5), 2.5% v/v Enzyme Storage Buffer+0.5% Tween 20, 0.2×SYBR Green I (from 20× solution in DMSO); 5% v/v Glycerol, dNTPs 0.2 mM each d(AGC)TP and 0.4 mM dUTP, 0.02 U/µl UNG, 2.75 mM Mg(OAc)$_2$, 0.2 mM Pyrophosphate, 10 nM DNA polymerase, 1E5 copies M13 mp18 DNA/20 µl reaction; and 0.2 µM each primer KAB77/KAB71. The composition of "Enzyme Storage Buffer" is: 20 mM Tris pH 8.0, 100 mM KCl, 0.1 mM EDTA, 1 mM DTT, 0.5% Tween 20, and 50% v/v glycerol.

The above reaction mixture can be varied. Non-limiting variations can include, for example, KOAc concentration between 20-120 mM, pyrophosphate concentration between 0.15-0.3 mM, and an Mg(OAc)$_2$ concentration between 2-4 mM. All reactions are performed in duplicate. Cycling conditions are: 2 minutes at 50° C. (to allow UNG sterilization); 92° C. for 1 minute; followed by 46 cycles of: denaturation at 92° C. for 15 second, then anneal/extend at 62° C. for 35 seconds.

Amplicon formation is then detected by increased relative fluorescence, using the conditions given above. When polymerases with efficient activation of blocked primers are used, detection of the amplicon will occur in earlier cycles than with inefficient polymerases. Agarose gel analysis can be used to verify that the expected 342 bp amplicon is the only detectable product made under these conditions.

In some embodiments, the rate at which the DNA polymerases are able to activate the blocked primer is estimated by the rate of change in fluorescence, after background subtraction. In order to distinguish extension-derived fluorescence from background fluorescence, parallel reactions can be included in which primer strand extension is prevented by leaving out the nucleotides from the reaction master mix. For each modified or mutant polymerase of the invention, activity can be estimated from the rate of increase in fluorescence, after background subtraction, and then compared to the rate of an otherwise identical DNA polymerase wherein the position at $X_6$ is T (SEQ ID NO:24) or the position at $X_{10}$ is T or A (SEQ ID NO:25) using the same reaction conditions.

B. Methods for Modifying or Mutating the DNA Polymerases

The production of the modified or mutant enzymes with, improved PAP ability or other desired properties may be accomplished by various processes including, e.g., site-directed mutagenesis, chemical modification, etc. More specifically, site-directed mutagenesis is generally accomplished by site-specific primer-directed mutagenesis. This technique is typically conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. In some embodiments, nucleic acid molecules encoding the unmodified form of the polymerase can be mutated by a variety of polymerase chain reaction (PCR) techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

By way of non-limiting example, the two primer system, utilized in the Transformer Site-Directed Mutagenesis kit from Clontech, can be employed for introducing site-directed mutants into a polynucleotide encoding an unmodified form of the polymerase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be mutated since this segment is of prime interest and the remaining map should be identical to the map of unmutagenized protein). The set of cleavage fragments is fractionated by, for example, microbore HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

C. Expression Vectors and Host Cells

Accordingly, the invention also provides for recombinant nucleic acids encoding any of the DNA polymerases described herein. In some embodiments, the invention comprises a vector having a nucleic acid encoding for a DNA polymerase disclosed herein. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant DNA polymerase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the polymerase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying a thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the mutant polymerase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)).

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a mutant DNA polymerase is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include CaPO$_4$ precipitation, liposome fusion, LIPOFECTIN®, electroporation, viral infection, and the like.

Prokaryotes are typically used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engi-* neering, *Principles and Methods* 12:275-296 (Plenum Publishing Corp., 1990); Hanahan et al., *Meth. Enzymol.*, 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

The DNA polymerases of the present invention are typically produced by culturing a host cell transformed with an expression vector containing a nucleic acid encoding the mutant DNA polymerase, under the appropriate conditions to induce or cause expression of the mutant DNA polymerase. Methods of culturing transformed host cells under conditions suitable for protein expression are well-known in the art (see, e.g., Sambrook et al., supra). Suitable host cells for production of the mutant polymerases from lambda pL promoter-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the mutant polymerase can be harvested and isolated. Methods for purifying the thermostable DNA polymerase are described in, for example, Lawyer et al., supra.

Once purified, the ability of the mutant DNA polymerases to extend primed templates can be tested in any of various known assays for measuring extension. For example, in the presence of primed template molecules (e.g., M13 DNA, etc.), an appropriate buffer, a complete set of dNTPs (e.g., dATP, dCTP, dGTP, and dTTP), and metal ion, DNA polymerases will extend the primers, converting single-stranded DNA (ssDNA) to double-stranded DNA (dsDNA). This conversion can be detected and quantified by, e.g., adding a dsDNA-binding dye, such as SYBR Green I. Using a kinetic thermocycler (see, Watson, et al. *Anal. Biochem.* 329:58-67, 2004, and also available from, e.g., Applied Biosystems, Stratagene, and BioRad), digital images of reaction plates can be taken (e.g., at 10-30 second intervals), thereby allowing the progress of the reactions to be followed. The amount of fluorescence detected can be readily converted to extension rates. Using such routine assays, extension rates of the mutants relative to the unmodified forms of polymerase can be determined.

III. Reaction Mixtures

The DNA polymerases of the present invention may be used for any purpose in which such enzyme activity is necessary or desired. In some embodiments the polymerases of the invention are used in various primer extension methods for amplification of a target nucleic acid. In certain embodiments, the primer extension methods involve the use of blocked primers, which requires the removal of the non-extendable 3'-nucleotide prior to primer extension (e.g. PAP). Conditions suitable for primer extension are known in the art. (See, e.g., Sambrook et al., supra. See also Ausubel et al., *Short Protocols in Molecular Biology* (4th ed., John Wiley & Sons 1999). Generally, a primer is annealed, i.e., hybridized, to a target nucleic acid to form a primer-template complex. The primer-template complex is contacted with the mutant DNA polymerase and free nucleotides in a suitable environment to permit the addition of one or more nucleotides to the 3' end of the primer, thereby producing an extended primer complementary to the target nucleic acid. The primer can include, e.g., one or more nucleotide analog(s). In addition, the free nucleotides can be conventional nucleotides, unconventional nucleotides (e.g., ribonucleotides or labeled nucleotides), or a mixture thereof. In some variations, the primer extension reaction comprises amplification of a target nucleic acid. Conditions suitable for nucleic acid amplification using a DNA polymerase and a primer pair are also known in the art (e.g., PCR amplification methods). (See, e.g., Sambrook et al., supra; Ausubel et al., supra; *PCR Applications. Protocols for Functional Genomics* (Innis et al. eds., Academic Press 1999). In other, non-mutually exclusive embodiments, the primer extension reaction comprises reverse transcription of an RNA template (e.g., RT-PCR). Use of the modified mutant polymerases of the present invention (which provide an improved extension rate) allow for e.g., the ability to perform primer extension reactions with relatively short incubation times, decreased enzyme concentrations, and/or increased product yield.

The invention also provides many different reaction mixtures that can be used in a wide variety of applications, particularly where it is desirable to remove terminator nucleotides (e.g. 2'-terminator nucleotides) from nucleic acids, polymerize nucleotides, and/or amplify nucleic acids. In some embodiments, for example, reaction mixtures are utilized in performing homogeneous amplification/detection assays (e.g., real-time PCR monitoring), or detecting mutations or genotyping nucleic acids. In certain embodiments, multiple primers and/or probes are pooled together in reaction mixtures for use in applications that involve multiplex formats. Many of these applications are described further below or are otherwise referred to herein.

In addition to the DNA polymerases described herein, reaction mixtures also generally include various reagents that are useful in performing, e.g., PAP, removal of terminator nucleotides from blocked oligonucleotides (e.g., to produce activated or extendible oligonucleotides), nucleotide polymerization, nucleic acid amplification and detection reactions (e.g., real-time PCR monitoring or 5'-nuclease assays), and the like. Exemplary types of these other reagents include, e.g., template or target nucleic acids (e.g., obtained or derived from essentially any source), pyrophosphate, light emission modifiers, buffers, salts, amplicons, glycerol, metal ions (e.g., $Mg^{++}$, etc.), dimethyl sulfoxide (DMSO), poly rA (e.g., as a carrier nucleic acid for low copy number targets), uracil N-glycosylase (UNG) (e.g., to protect against carry-over contamination). In some kinetic PCR-related applications, reaction mixtures also include probes that facilitate the detection of amplification products. Examples of probes used in these processes include, e.g., hybridization probes, 5'-nuclease probes, and/or hairpin probes. Nucleic acid amplification and detection as well as other methods are also described further below.

Reaction mixtures are generally produced by combining selected nucleotides, primers, and/or probes, as described above, with quantities of the other reagents that are sufficient for performing the particular application that is selected. The quantities of reagents to be included in a given reaction mixture will be apparent to persons of skill in the art in view of the selected method to be performed.

IV. Methods of Using the Modified DNA Polymerases

The invention also provides methods of using the modified polymerases described herein. In some embodiments, for example, these polymerases are used to perform assays that involve the detection of target nucleic acids, e.g., to provide diagnostic, genetic, or other information about subjects from which these targets were derived. These aspects are also illustrated in the examples provided herein.

The polymerases described herein are optionally used or adapted for use in essentially any application that involves the removal of a terminator nucleotide from the 3'-end of a nucleic acid, e.g., via the process of pyrophosphorolysis. Examples of nucleic acid-related types of applications, include the analysis of the structure and conformation of nucleic acids, real-time PCR assays, and SNP detection (Myakishev et al. (2001) *Genome Res* 11:163-169; Lee et al. (1999) *Biotechniques* 27:342-349; Thelwell et al. (2000) *Nucleic Acids Res* 28:3752-3761; Whitcombe et al. (1999) *Nat. Biotechnol.* 17:804-807, Heid et al. (1996) *Genome Res.* 6:986-994, Nazarenko et al. (1997) *Nucleic Acids Res.* 25:2516-2521); detection of nucleic acid hybridization (Parkhurst et al. (1995) *Biochemistry* 34:285-292; Tyagi et al. (1996) *Nat Biotechnol* 14:303-308; Tyagi et al. (1998) *Nat Biotechnol* 16:49-53; Sixou et al. (1994) *Nucleic Acids Res* 22:662-668; and Cardullo et al. (1988) *Proc Natl Acad Sci USA* 85:8790-8794); primer-extension assays for detecting mutations (Chen et al. (1997) *Proc Natl Acad Sci USA* 94:10756-10761); and automated DNA sequencing (Woolley et al. (1995) *Anal Chem* 67:3676-3680, Hung et al. (1998) *Anal Biochem* 255:32-38, and Ju et al. (1995) *Proc Natl Acad Sci USA* 92:4347-4351). The modified enzymes can also be used in various pyrophosphorolysis activated polymerization methods as described in, e.g., U.S. Pat. Nos. 7,033,763; 6,534,269; and U.S. patent application Ser. No. 10/798,844.

To further illustrate, examples of general types of nucleic acid analysis technologies that can be used or adapted for use to analyze target nucleic acids in or from, e.g., the reactions mixtures of the invention include various nucleic acid amplification assays. A common characteristic among nucleic acid amplification assays is that they are typically designed to amplify nucleic acid sequences that are specific for the organism being detected. Nucleic acid amplification tests generally have greater sensitivity than other approaches to nucleic acid analysis. This sensitivity, which is further improved with the use of the DNA polymerases described herein, is typically attributable to their ability to produce a positive signal from as little as a single copy of a perfectly matched primer:template complex. Amplification methods that are optionally utilized or adapted to detect target nucleic acids include, e.g., various polymerase, ligase, or reverse-transcriptase mediated amplification methods, such as the polymerase chain reaction (PCR), the ligase chain reaction (LCR), and/or the reverse-transcription PCR (RT-PCR). Additional details regarding the use of these and other amplification methods and various approaches to sample preparation for these assays can be found in any of a variety of standard texts, including, e.g., Berger, Sambrook, Ausubel 1 and 2, and Innis, supra.

Various commercial nucleic acid amplification assays that are optionally adapted for use with the reagents and methods of the invention generally differ in their amplification methods and their target nucleic acid sequences. Examples of these commercial tests include hybridization probe assays (e.g., using the LightCycler® system) and the AMPLICOR® and COBAS AMPLICOR® assays (Roche Diagnostics Corporation, Indianapolis, Ind., USA), which use polymerase chain reactions (PCR); the LCx® test (Abbott Laboratories, Abbott Park, Ill., USA), which uses ligase chain reactions (LCR); the BDProbeTec™ ET test (Becton, Dickinson and Company, Franklin Lakes, N.J., USA), which uses strand displacement amplification (SDA); and the APTIMA™ assay (Gen-Probe, Inc., San Diego, Calif., USA), which uses transcription-mediated amplification (TMA).

In certain embodiments, for example, 5'-nuclease probes are utilized in various 5'-nuclease reactions. Many 5'-nuclease assays are well known to those of skill in the art. Examples of such reactions are also described in, e.g., U.S. Pat. Nos. 6,214,979; 5,804,375; 5,487,972; and 5,210,015.

To briefly illustrate, in a 5'-nuclease reaction, a target nucleic acid is contacted with a primer and a probe (e.g., a 5'-nuclease probe) under conditions in which the primer and probe hybridize to a strand of the target nucleic acid. The target nucleic acid, primer and probe are also contacted with a nucleic acid polymerase having 5' to 3' nuclease activity. Nucleic acid polymerases possessing 5' to 3' nuclease activity can cleave the probe hybridized to the target nucleic acid downstream of the primer. The 3' end of the primer provides the initial binding site for the polymerase. The bound polymerase cleaves fragments from the probe upon encountering the 5' end of the probe.

The primer and probe can be designed so that they anneal in close proximity on the target nucleic acid such that binding of the nucleic acid polymerase to the 3' end of the primer puts it in contact with the 5' end of the probe in the absence of primer extension. The term "polymerization-independent cleavage" refers to this process. Alternatively, if the primer and probe anneal to more distantly spaced regions of the target nucleic acid, polymerization typically occurs before the nucleic acid polymerase encounters the 5' end of the probe. As the polymerization continues, the polymerase progressively cleaves fragments from the 5' end of the probe. This cleavage continues until the remainder of the probe has been destabilized to the extent that it dissociates from the template molecule. The term "polymerization-dependent cleavage" refers to this process.

One advantage of polymerization independent cleavage lies in the elimination of the need for amplification of the nucleic acid. Provided the primer and probe are adjacently bound to the nucleic acid, sequential rounds of probe annealing and cleavage of fragments can occur. Thus, a sufficient amount of fragments can be generated, making detection possible in the absence of polymerization.

In either process, a sample is provided which is thought to contain the target nucleic acid. The target nucleic acid contained in the sample may be first reverse transcribed into cDNA, if necessary, and then denatured, using any suitable denaturing method, including physical, chemical, or enzymatic methods, which are known to those of skill in the art. An exemplary physical approach to effect strand separation involves heating the nucleic acid until it is completely (>99%) denatured. Typical heat denaturation involves temperatures ranging from about 85° C. to about 105° C. (typically from about 85° C. to about 98° C., and more typically from about 85° C. to about 95° C.), for periods of time ranging from about 1 second to about 10 minutes (e.g., from few seconds to about 1 minute). As an alternative to denaturation, the nucleic acid may exist in a single stranded form in the sample, such as when the sample comprises single-stranded RNA or DNA viruses.

The denatured target nucleic acid strand is typically incubated with a primer and a probe under hybridization conditions that permit the primer and probe to bind to the target nucleic acid strand. In some embodiments, two primers can be used to amplify the target nucleic acid. The two primers are typically selected so that their relative positions along the target nucleic acid are such that an extension product synthesized from one primer, when the extension product is separated from its template (complement), serves as a template for the extension of the other primer to yield a replicate strand of defined length.

Because the complementary strands are typically longer than either the probe or primer, the strands have more points of contact and thus a greater chance of binding to each other over a given period of time. Accordingly, a high molar excess of probe and primer is typically utilized to favor primer and probe annealing over template strand reannealing. In multiplexing formats, multiple probes are typically used in a single reaction vessel to simultaneously detect multiple target nucleic acids.

Primers are generally of sufficient length and complementarity so that they selectively bind to target nucleic acids under selected conditions to permit polymerization-independent cleavage or polymerization-dependent cleavage to proceed. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the primer typically includes about 15 to 30 nucleotides, although it may contain more or fewer nucleotides.

The probe is generally annealed to its complementary target nucleic acid before the nucleic acid polymerase encounters that region of the target nucleic acid, thereby permitting the 5' to 3' nuclease activity of the enzyme to cleave fragments from the probe. To enhance the likelihood that the probe will anneal to the target nucleic acid before the polymerase reaches this region of hybridization, a variety of techniques may be utilized. For example, short primers generally require cooler temperatures to form sufficiently stable hybrid complexes with the nucleic acid. Therefore, the probe can be designed to be longer than the primer so that the probe preferentially anneals to the target nucleic acid at higher temperatures relative to primer annealing. To further illustrate, the nucleotide composition of the probe can be chosen to have greater G/C content and, consequently, greater thermal stability than the primer. Optionally, modified nucleotides can be incorporated into primers or probes to effect either greater or lesser thermal stability in comparison to primers or probes having only unmodified nucleotides. In some embodiments, the primers contain a terminator nucleotide at the 3'-end. The thermocycling parameters can also be varied to take advantage of the differential thermal stability of the probe and primer. For example, following a thermocycling denaturation step, an intermediate temperature may be introduced which permits probe binding, but not primer binding. Thereafter, the temperature can be further reduced to permit primer annealing. To preferentially favor binding of the probe before the primer, a high molar excess of probe to primer concentration can also be used. Such probe concentrations are typically in the range of about 2 to about 20 times higher than the respective primer concentration, which is generally about 0.5 to $5 \times 10^{-7}$ M.

Template-dependent extension of primers can be catalyzed using the DNA polymerases described herein, in the presence of adequate amounts of the four deoxyribonucleoside triphosphates (dATP, dGTP, dCTP, and dTTP) or analogs in a reaction mixture that also includes appropriate salts, metal cations, and buffers. Reaction mixtures are described further above. The reaction conditions for catalyzing DNA synthesis with these DNA polymerases are well known in the art. In some embodiments, in addition to improved PAP ability, the DNA polymerase has 5'-3' nuclease activity to efficiently cleave the probe and release labeled fragments so that a detectable signal is directly or indirectly generated.

The products of the synthesis are generally duplex molecules that include the template strands and the primer extension strands. Byproducts of this synthesis are probe fragments, which can include a mixture of mono, di and larger nucleotide fragments. Repeated cycles of denaturation, probe and primer annealing, and primer extension and probe cleavage result in the exponential accumulation of the region defined by the primers and the exponential generation of labeled fragments. Sufficient cycles are run to achieve a detectable amount of probe fragments, which is generally several orders of magnitude greater than background signal.

In certain embodiments, PCR reactions are carried out as an automated process, which utilizes a thermostable DNA polymerase enzyme as described herein. In this process the reaction mixture is cycled through a denaturing step, a probe and primer annealing step, and a synthesis step in which cleavage and displacement occur concurrently with primer dependent template extension. In some embodiments, the methods described herein are performed using a system. Optionally, thermal cyclers, such as those commercially available from, e.g., Applied Biosystems (Foster City, Calif., USA), which are designed for use with thermostable enzymes, such as the DNA polymerases of the present invention.

Essentially, the DNA polymerase enzymes of the present invention can be used with any available method for detecting and amplifying target nucleic acids. Common approaches include real-time amplification detection with 5'-nuclease probes, hybridization probes, or hairpin probes (e.g., molecular beacons), detection of labels incorporated into the amplification primers or the amplified nucleic acids themselves, e.g., following electrophoretic separation of the amplification products from unincorporated labels, hybridization based assays (e.g., array based assays), and/or detection of secondary reagents that bind to the nucleic acids. These general approaches are also described in, e.g., Sambrook, and Ausubel 1 and 2, supra.

In other illustrative embodiments of using the modified polymerases described herein, include the use of labeled primers to effect real-time target nucleic acid detection. Primer-based approaches to real-time target nucleic acid detection that can be adapted for use with the DNA polymerases described herein are also described in, e.g., Huang et al. (2004) *Biotechnol Lett.* 26(11):891-895, Asselbergs et al. (2003) *Anal Biochem.* 318(2):221-229, and Nuovo et al. (1999) *J Histochem Cytochem.* 47(3):273-280.

V. Kits

The present invention also provides kits for extending nucleic acids. Generally, the kit includes at least one container providing a DNA polymerase of the invention as described herein. In certain embodiments, the kit further includes one or more additional containers providing one or more additional reagents. For example, in specific variations, the one or more additional containers provide free nucleotides; a buffer suitable for PAP; and/or a primer hybridizable, under PAP conditions, to a predetermined polynucleotide template. In some embodiments, the primer has a non-extendable terminator nucleotide at the 3'-terminal end. In some embodiments, the terminator nucleotide includes at least one label (e.g., a radioisotope, a fluorescent dye, a mass-modifying group, or the like). In some embodiments, the kit further includes one or more extendible nucleotides and optionally, at least one of the extendible nucleotides comprises a label (e.g., a radioisotope, a fluorescent dye, a mass-modifying group, or the like). Optionally, the kit further includes at least one pyrophosphatase (e.g., a thermostable pyrophosphatase, etc.). Typically, the kit also includes a set of instructions for extending the nucleic acid with the DNA polymerases disclosed herein. In certain embodiments, the kit further includes a template nucleic acid and the primer nucleic acid, which primer nucleic acid is complementary to at least a subsequence of the template nucleic acid. Optionally, the template nucleic acid or the primer nucleic acid is attached to a solid support. In some of these embodiments, the primer comprises a label, such as a radioisotope, a fluorescent dye, a mass-modifying group, or the like.

All patents, patent applications, and other publications cited in this application are hereby incorporated by reference in their entirety.

EXAMPLES

The following examples are included for illustration purposes and are not intended to be construed as a limitation on the invention in any way. It will be appreciated by those of skill in the art that the techniques disclosed herein and in the examples that follow represent techniques discovered by the inventor to function well in the practice of the invention, and can thus be considered to represent preferred modes for practice of the invention. However, those skilled in the art will also recognize, in light of the present disclosure, that many changes can be made to the specific embodiments disclosed herein and obtain similar results without departing from the spirit or scope of the invention.

Example 1

Identification and Characterization of Mutant DNA Polymerases

This example shows the identification and characterization of mutant DNA polymerases with improved activation of 2'-$PO_4$-blocked primer. A mutation in the CS-family polymerases was identified that provides improved ability to remove the blocking group from a 2'-phosphate-blocked primer when the primer is annealed to its perfectly complementary template. In brief, the steps in this screening process included library generation, expression and partial purification of the mutant enzymes, screening of the enzymes for the desired property, sequencing purification, and further characterization of selected mutants, and generation, purification, and characterization of the mutations in different genetic backgrounds. Each of these steps is described further below.

The mutation identified by this process was T606S. This mutation was then placed in related CS-family polymerases, including G46E L329A E678G CS5 (GLE-CS5) and G46E L329A D640G S671F E678G CS5 (GLDSE-CS5). The resulting mutant polymerases were characterized by analyzing their performance in a series of Kinetic Thermal Cycling (KTC) experiments.

The identified mutation, T606S, resulted in an improved ability to activate and extend 2'-$PO_4$-blocked primer when annealed to a perfectly matched template, in the context of the E678G mutation, which allowed for the incorporation of ribonucleotides and other 2'-modified nucleotides, but which also resulted in an impaired ability to extend primed templates. The S671F and D640G, as well as the Q601R, and I669F mutations, ameliorate this property of impaired primer extension ability.

Clonal Library generation: The polymerase domain of CS5 E678G DNA polymerase was subjected to error-prone PCR between the Bgl II and Hind III restriction sites. The primers used for this amplification are given below:

```
Forward Primer:
5'- GCAGCGAACTACTCCTGTGA-3';       (SEQ ID NO:31)
and,

Reverse Primer:
5'-ACATCCACTTCGAGCGGCACTGA-3'.     (SEQ ID NO:32)
```

PCR was performed using a range of $Mg^{+2}$ concentrations from 1.8-3.5 mM, in order to generate libraries with a corresponding range of mutation rates. Buffer conditions were: 50 mM Bicine pH 8.2, 115 mM KOAc, 8% w/v glycerol, 0.2 mM each dNTPs, and 0.2×SYBR Green I. A GENEAMP® AccuRT Hot Start PCR enzyme was used at 0.15 U/µl. Starting with 5×10$^5$ copies of linearized CS5 E678G plasmid DNA/reaction volume of 50 µl, 30 cycles of amplification were performed, using an annealing temperature of 60° C. for 15 seconds, an extension temperature of 72° C. for 45 seconds, and a denaturation temperature of 95° C. for 15 seconds.

The resulting amplicon was purified over a Qiaquick spin column (Qiagen, Inc., Valencia, Calif., USA) and cut with Bgl II and Hind III, then re-purified. A vector plasmid, a modification of G46E L329A CS5 carrying a large deletion in the polymerase domain between the BglII and HindIII sites, was prepared by cutting with the same two restriction enzymes and treating with calf intestinal phosphatase (CIP). The cut vector and the mutated insert were mixed at different ratios and treated with T4 ligase overnight at 15° C. The ligations were purified and transformed into E. coli strain LK3 by electroporation.

Aliquots were plated on ampicillin-selective medium in order to determine the number of unique transformants in each transformation. Transformations with the most unique transformants at each mutagenesis rate were stored at −70 to −80° C. in the presence of glycerol as a cryo-protectant.

Each library was then spread on large format ampicillin-selective agar plates. Individual colonies were transferred to 384-well plates containing 2× Luria broth with ampicillin and 10% w/v glycerol using an automated colony picker (QPix2, Genetix Ltd). These plates were incubated overnight at 30° C. to allow the cultures to grow, then stored at −70 to −80° C. The glycerol added to the 2× Luria broth was low enough to permit culture growth and yet high enough to provide cryo-protection. Several thousand colonies at several mutagenesis ($Mg^{+2}$) levels were prepared in this way for later use.

Extract library preparation Part 1—Fermentation: From the clonal libraries described above, a corresponding library of partially purified extracts suitable for screening purposes was prepared. The first step of this process was to make small-scale expression cultures of each clone. These cultures were grown in 96-well format; therefore there were 4 expression culture plates for each 384-well library plate. Next, 0.5 µl from each well of the clonal library plate was transferred to a well of a 96 well seed plate, containing 150 µl of Medium A (see Table 2 below). The seed plate was then shaken overnight at 1150 rpm at 30° C., in an iEMS plate incubater/shaker (ThermoElectron). Seed cultures were then used to inoculate the same medium, this time inoculating 2.5 µl into 270 µl Medium A in large format 96 well plates (Nunc #267334). These plates were incubated overnight at 37° C. The expression plasmid contained transcriptional control elements which allow for expression at 37° C. but not at 30° C. After overnight incubation, the cultures expressed the clone protein at typically 1-10% of total cell protein. The cells from these cultures were harvested by centrifugation. These cells were either frozen (−70° C.) for at least 2 hours before further processing, described below.

TABLE 2

| Medium A (Filter-sterilized prior to use) | |
|---|---|
| Component | Concentration |
| $MgSO_4 \cdot 7H_2O$ | 0.2 g/L |
| Citric acid·$H_2O$ | 2 g/L |

TABLE 2-continued

Medium A (Filter-sterilized prior to use)

| Component | Concentration |
|---|---|
| $K_2HPO_4$ | 10 g/L |
| $NaNH_4PO_4 \cdot 4H_2O$ | 3.5 g/L |
| $MgSO_4$ | 2 mM |
| Casamino acids | 2.5 g/L |
| Glucose | 2 g/L |
| Thiamine•HCl | 10 mg/L |
| Ampicillin | 100 mg/L |

Extract library preparation Part 2—Extraction: Cell pellets from the fermentation step were resuspended in 25 µl Lysis buffer (Table 3 below). Note that the buffer contains lysozyme to assist in cell lysis, and a nuclease ("benzonase") to remove both RNA and DNA from the extract. The plates were shaken at 1150 rpm at 37° C. for 1-2 hours. Ammonium sulfate was added (2 µl of a 2M solution), and the extracts were transferred to 384-well thermocycler plates. The plates were frozen overnight at −70° C. They were then incubated at 37° C. for 15 minutes, then at 75° C. for 15 minutes in a thermocycler (ABI 9700), in order to precipitate and inactivate contaminating proteins, including the exogenously added enzymes. The plates were centrifuged at 3000×g for 15 minutes and the supernatants transferred to a fresh 384 well thermocycler plate. These extract plates were frozen at −20° C. for later use in screens. Each well contained about 0.5-3 µM of the mutant polymerase enzyme. In addition, the extract plates were diluted 10-fold into a buffer consisting of 20 mM Tris pH 8.0, 0.1 mM EDTA, 100 mM KCl, and 0.2% Tween 20. These diluted extracts were then used for screening for improved PAP mutants, as described below.

TABLE 3

Lysis Buffer

| Component | Concentration or Percentage |
|---|---|
| Benzonase (Novagen #70584 | 1X |
| Lysozyme (from powder) | 1 mg/ml |
| Benzonase (Novagen # 71205) | 125 U/ml |

Screening Extract Libraries for PAP mutants: Diluted extracts were used in two separate extension rate determinations. In the first assay, M13 mp18 single-stranded DNA (M13 DNA), primed with an oligonucleotide having the following sequence:

5'-GGGAAGGGCGATCGGTGCGGGCCTCTTCGC-3' (SEQ ID NO:33)

was used as the template. Extract (0.5 µl) was added to 13 µl reaction master mix containing 1 nM primed M13 template in 384 well PCR plates. Extension of the primed template was monitored every 20 seconds at 64° C. in a modified kinetic thermocycler using a CCD camera. The reaction master mix was: 100 mM Tricine pH 8.0, 20 mM KOAc, 3 mM $Mg(OAc)_2$, 2.5% Enzyme Storage Buffer, 1×SYBR Green I (Molecular Probes), and 0.1 mM each dATP, dCTP, dGTP, and dTTP. ("Enzyme Storage Buffer" is composed of 20 mM Tris pH 8.0, 100 mM KCl, 0.1 mM EDTA, 1 mM DTT, 0.5% Tween 20, and 50% v/v glycerol.) In order to distinguish extension-derived fluorescence from background fluorescence, parallel wells were included in the experiment in which primer strand extension was prevented by leaving out the nucleotides from the reaction master mix. For each extract, polymerase activity was estimated from the rate of increase in fluorescence, after background subtraction.

In order to find mutant enzymes which have improved rate of activation of 2'-$PO_4$-blocked primers, a second set of extension assays was performed on each extract. In this second set of assays, a pre-annealed oligo duplex substrate was substituted for the primed M13 template. The primer strand had the sequence: CGCCTGGTCTGTACACCGTTCE (SEQ ID NO:34), where E=2'$PO_4$-dA, and the template strand had the sequence:

(SEQ ID NO:35)
CAACTTTGAAAGAGGACAGATGAACGGTQTACAQACCAQGCGP, where Q=7-deaza-dG, and P=3' $PO_4$. The 7-deaza-dG residues in the templating strand result in reduced background fluorescence. This oligo duplex was added to the reaction mix at 100 nM. Additionally pyrophosphate was added to 0.5 mM. Other than the change of substrate and the addition of pyrophosphate, conditions were identical to the M13 extension reaction described above. The rate at which extracts were able to activate the blocked primer was estimated by the rate of change in fluorescence, after background subtraction. This rate was then compared to the activity on M13 template. The ratio of these two rates was used to determine which mutants have relatively high 2'-$PO_4$-blocked primer activation activity.

Figure 5:
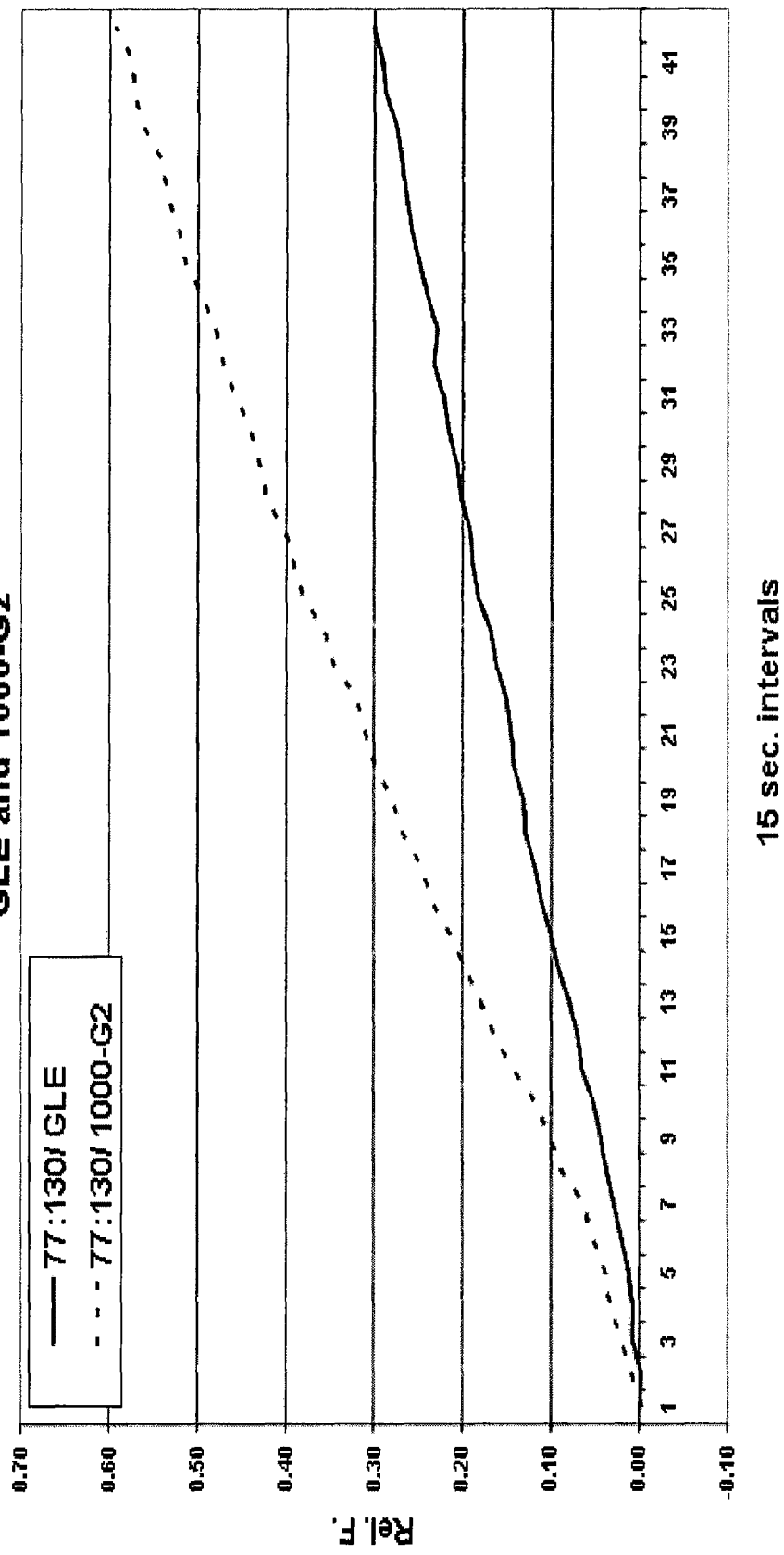
FIG. 5 shows that the mutant polymerase can activate the blocked primer more rapidly than the parental wild-type.
Figure 6:
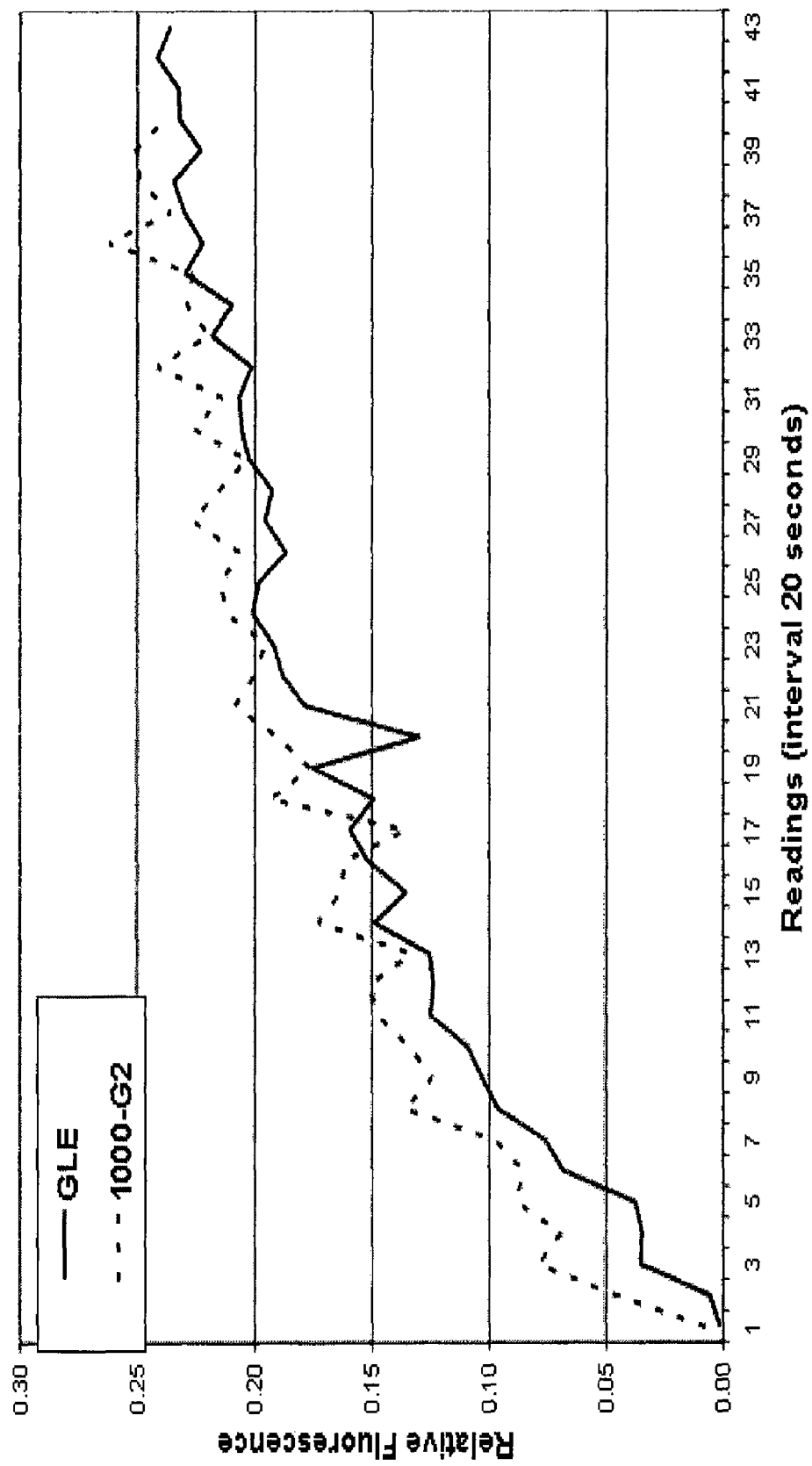
FIG. 6 shows that the mutations did not have an adverse effect on the ability of the polymerase to extend an unblocked primer.

Several thousand extracts were screened in this manner. Typical results are shown in FIG. 4. One extract, labeled "1AS-G2", stood out as having high activity on the blocked oligo duplex (see, FIG. 4). This clone, re-named "1000-G2", was chosen for further study. After recovering the clone from the clonal library, the DNA sequence of the mutated region of the clone was analyzed by Sanger sequencing and found to carry three mutations relative to the parental sequence. These mutations, and corresponding the amino acid sequence changes, were: A7161G (K570R); A7268T (T606S); and T7285 (silent mutation, no amino acid change). In a parallel study highly purified enzyme was produced in shake flask culture and the concentration determined by gel-based densitometry. This purified enzyme directly was compared with the parental enzyme, G46E L329A E678G CS5, or "GLE", for the ability to activate the same blocked oligo duplex used in the screen and for the ability to extend primed M13. These assays were performed under conditions similar to those used in the screen, utilizing SYBR Green I detection of double stranded DNA, except that they were done at identical enzyme concentration and with multiple replicates, to increase precision. The extension assays showed that the mutant is able to activate the blocked primer more rapidly than the parental type (FIG. 5), and further that the mutations had no effect on normal extension of a primed DNA template (FIG. 6)

Figure 7:
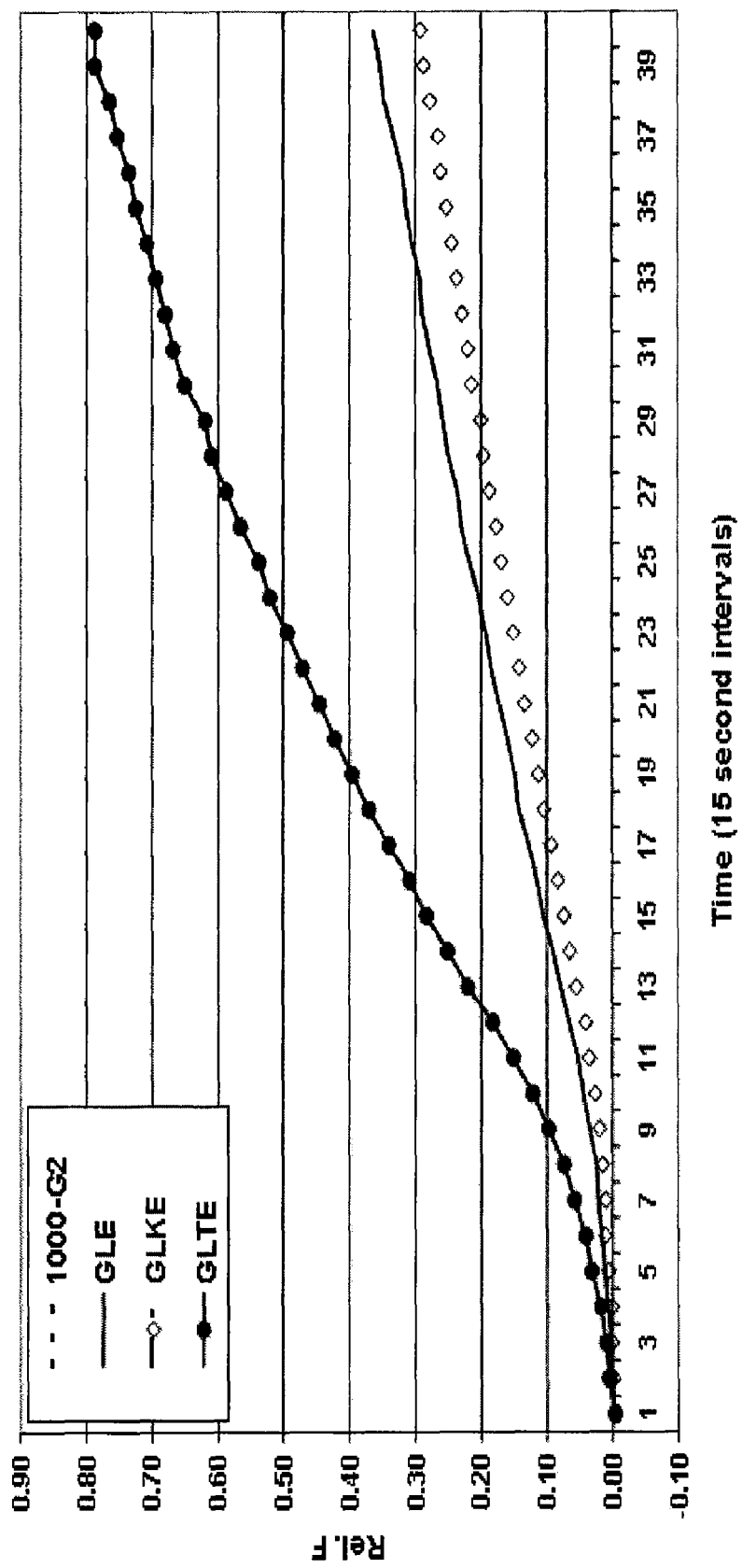
FIG. 7 shows that the T606 mutation was responsible for the improved activation of the blocked primer in the 1000-G2 clone.

In order to determine which of the two amino acid changes in 1000-G2 is responsible for the observed phenotype, the two mutations were moved separately into the parental background, by in vitro mutagenesis of the parental plasmid, using overlap PCR. Mutant with the genotypes G46E L329A K570R E678G CS5 ("GLKE") and G46E L329A T606S E678G CS5 ("GLTE") were created. The mutants were purified to homogeneity, quantified, and run in the blocked oligo duplex assay. The results (FIG. 7) indicate that the mutation T606S is solely responsible for the improved activation of 2'-$PO_4$-blocked primers seen with clone 1000-G2 in the original screen.

Figure 8:
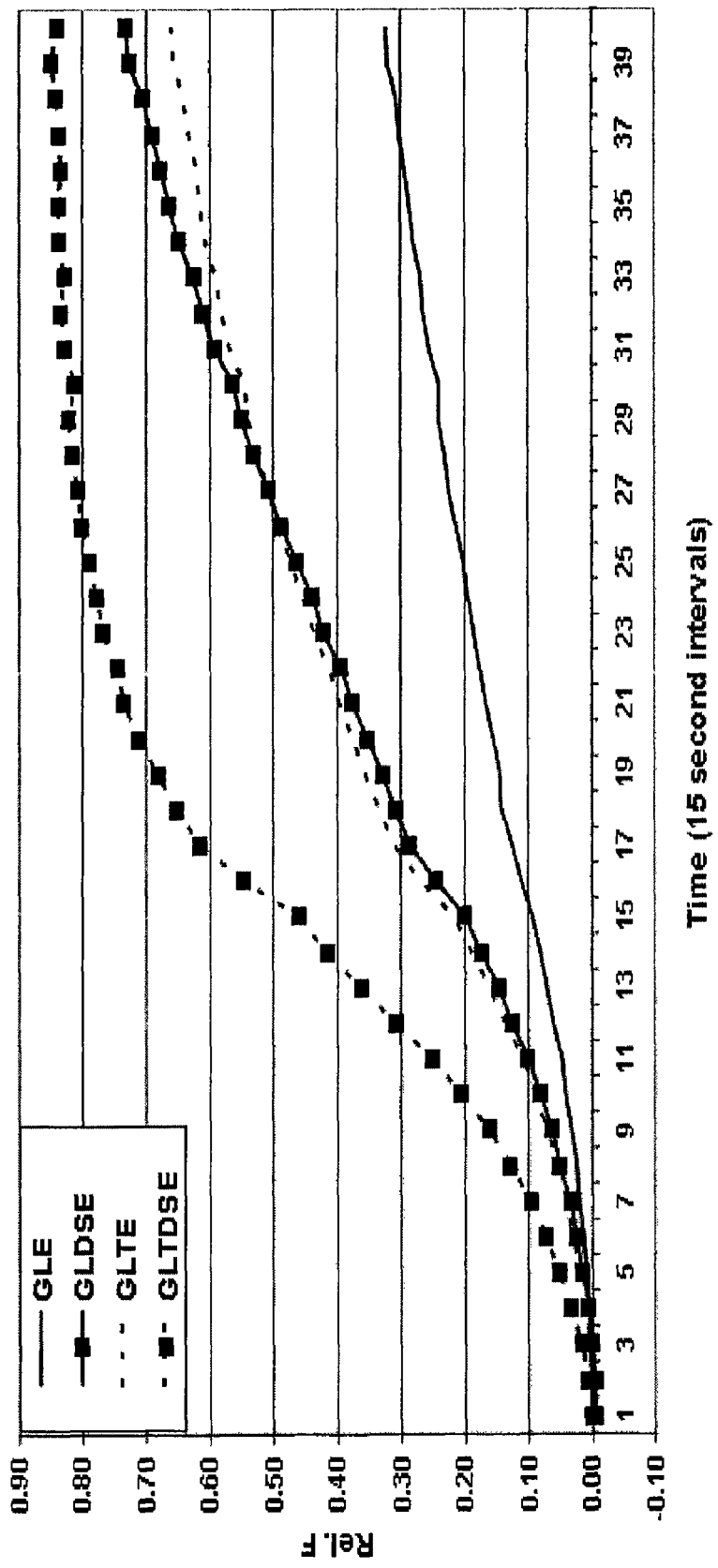
FIG. 8 shows that the GLTDSE mutant is faster than either of its parent clones in activating a blocked primer.

Certain other mutations in CS5 DNA polymerase have been discovered which enhance the properties of that enzyme in certain applications. Two of these mutations, D640G and S671F, when combined, result in significantly faster extension rate and improved performance in PCR applications, particularly when the polymerase also carries the ribo-incorporating mutation E678G. In order to see if performance of GLTE would be enhanced by these extension rate mutations, a clone was created with the genotype G46E L329A T606S D640G S671F E678G CS5 ("GLTDSE"), by a simple restriction fragment swap between GLTE and GLQDSE, using the vector unique restriction sites SapI and NdeI. After purification/quantification, this enzyme was run in the blocked oligo duplex assay described above. The results (FIG. 8) indicate that GLTDSE is faster than either of its parent clones in activating this 2'-PO$_4$-blocked primed oligo duplex.

Example 2

Use of T606S Mutants in PAP-PCR

This examples demonstrates the use of the T606S mutants in PAP-PCR. Pyrophosphorolysis Activated Polymerization, referred to here as "PAP-PCR", is a modification of the PCR process which enhances specificity by requiring that a blocked primer binds to a perfectly matched template molecule before that primer is activated by pyrophosphorolysis. This "specificity check" is effective at each cycle of PCR, because if an error is made, and pyrophosphorolysis occurs on a mismatched primer, the resulting extension product will still be mismatched in subsequent round of extension, and hence will not result in accumulation of a mismatched amplicon.

We tested the ability of one of our T606S mutants to perform PAP-PCR in a model system which utilized M13 mp18 as the template. The primers used had the sequences:

```
KAB77:   CGCCTGGTCTGTACACCGTTCE,   (SEQ ID NO:26)
where E = 2'PO4-dA,
and

KAB71:   GGAACGAGGGTAGCAACGGCTACE, (SEQ ID NO:27)
where E = 2'PO4-dA.
```

Together the two primers are expected to make a 342 bp amplicon from M13 template. Note that both primers are blocked with a 2'-PO$_4$ group at the 3'-end, and cannot be extended until that group is removed by pyrophosphorolysis of the terminal dA residue. Previous observations indicated that the rate of activation by pyrophosphorolysis of different 2'-PO$_4$-blocked primers varied, and that KAB77 activation was relatively slow, requiring long extension times of up to 5 minutes in the PCR to achieve efficient amplification. In contrast, we have found that using the GLTDSE CS5 DNA polymerase mutant resulted in rapid and efficient amplification from M13 template and the primers listed above.

The reaction conditions used are listed in Table 4 below:

Table 4 Reaction Conditions

TABLE 4

| Reaction Conditions | |
|---|---|
| Tricine pH 7.5 | 50 mM |
| KOAc pH 7.5 | 80 mM |
| Enzyme Storage Buffer + 0.5% Tween 20 | 2.5% v/v |
| SYBR Green I | 0.2X (from 20X solution in DMSO) |
| Glycerol | 5% v/v |
| dNTPs | 0.2 mM each d(AGC)TP, 0.4 mM dUTP |
| UNG | 0.02 U/µl |
| Mg(OAc)$_2$ | 2.75 mM |
| Pyrophosphate | 0.2 mM |
| GLTDSE DNA polymerase | 10 nM |
| M13mp18 DNA | 1E5 copies/20 µl reaction |
| Primers KAB77/KAB71 | 0.2 µM each |

The composition of "Enzyme Storage Buffer" is given above in Example I. SYBR Green I allowed detection of product accumulation by fluorescence in a 384-well kinetic thermocycler. Use of dUTP and UNG allows for amplicon sterilization to prevent contamination from previous PCR experiments.

An experiment was performed using this reaction mixture, in which the KOAc concentration was varied between 20-120 mM, the pyrophosphate concentration was varied between 0.15-0.3 mM, and the Mg(OAc)$_2$ concentration was varied between 2-4 mM. All reactions were performed in duplicate. Cycling conditions were: 2 minutes at 50° C. (to allow UNG sterilization); 92° C. for 1 minute; followed by 46 cycles of: denaturation at 92° C. for 15 second, then anneal/extend at 62° C. for 35 seconds.

We detected amplicon formation by increased relative fluorescence at a Ct of 21.4 cycles, using the conditions given in the Table above. This is indicative that very efficient amplification was achieved, given the input copy number and the relatively short extension time of only 35 seconds. Agarose gel analysis indicated that the expected 342 bp amplicon was the only detectable product made under these conditions. Additionally, we found that reaction conditions could be varied somewhat with only insignificant cycle delays in Ct. For instance, allowing for a Ct delay of 1 cycle or less, the KOAc concentration could be varied from 60-100 mM; and pyrophosphate could be varied between 0.15-0.3 mM; and the Mg(OAc)$_2$ could be varied between 2.5-3.5 mM. This indicates that the GLDTSE CS5 DNA polymerase is capable of performing rapid and efficient PAP-PCR with these blocked primers under a reasonably wide range of reaction conditions.

What is claimed is:

1. A DNA polymerase, comprising R-$X_1$-$X_2$-$X_3$-K-L-$X_4$-$X_5$-$X_6$-Y-$X_7$-$X_8$-$X_9$-$X_{10}$-$X_{11}$, wherein
   $X_1$ is selected from the group consisting of E, Q, G, K, and T,
   $X_2$ is L, I, Y,
   $X_3$ is selected from the group consisting of T, M, D, S, G, A, Q, and L,
   $X_4$ is K, R, Q,
   $X_5$ is N, S, G,
   $X_6$ is S,
   $X_7$ is selected from the group consisting of V, I, L, A, T,
   $X_8$ is D or E,
   $X_9$ is selected from the group consisting of P, A, G, K, T, and S,
   $X_{10}$ is L or I,
   $X_{11}$ is P or L (SEQ ID NO:60);
   wherein the polymerase has improved pyrophosphorolysis activated polymerization (PAP) relative to an otherwise identical polymerase where $X_6$ is T.

2. The DNA polymerase of claim 1, wherein the polymerase has a faster rate of extending blocked primer KAB77 (SEQ ID NO:27) relative to an otherwise identical polymerase where $X_6$ is T.

3. The DNA polymerase of claim 1, wherein the polymerase comprises a chimeric polymerase.

4. A recombinant nucleic acid encoding the DNA polymerase according to claim 1.

5. An expression vector comprising the recombinant nucleic acid of claim 4.

6. A host cell comprising the expression vector of claim 5.

7. A reaction mixture comprising a polynucleotide template, at least one primer having a non-extendable nucleotide at the 3'-end, and a DNA polymerase of claim 1.

8. The reaction mixture of claim 7, wherein the non-extendable nucleotide is a 2'-terminator nucleotide.

9. A method of producing a DNA polymerase, said method comprising:
   culturing the host cell of claim 6 under conditions suitable for expression of the nucleic acid encoding the DNA polymerase.

10. A method for achieving pyrophosphorolysis activated polymerization, comprising:
    contacting a DNA polymerase according to claim 1 with a primer, a polynucleotide template, and free nucleotides, wherein the 3'-end of the primer is blocked with a non-extendable nucleotide,
    and under conditions suitable for pyrophosphorolysis of the non-extendable nucleotide at the 3'-end of the primer, followed by extension of the primer, thereby achieving pyrophosphorolysis activated polymerization.

11. A method for conducting primer extension, comprising:
    contacting a DNA polymerase according to claim 1 with a primer, a polynucleotide template, and free nucleotides under condition suitable for extension of the primer, thereby producing an extended primer.

12. The method of claim 10, wherein the polynucleotide template is a DNA.

13. The method of claim 11, wherein the polynucleotide template is a DNA.

14. The method of claim 10, wherein the free nucleotides comprise unconventional nucleotides.

15. The method of claim 11, wherein the free nucleotides comprise unconventional nucleotides.

16. The method of claim 14, wherein the unconventional nucleotides comprise labeled nucleotides.

17. The method of claim 15, wherein the unconventional nucleotides comprise labeled nucleotides.

18. The method of claim 10, wherein the non-extendable nucleotide is a 2'-terminator nucleotide.

19. The method of claim 18, wherein the 2'-terminator nucleotide comprises a 2'-monophosphate-3'-hydroxyl-5'-triphosphate nucleoside.

20. The method of claim 10, wherein the non-extendable nucleotide is a di-deoxynucleotide.

21. A kit for performing pyrophosphorolysis activated polymerization, comprising:
at least one container providing a DNA polymerase according to claim 1.

22. The kit according to claim 21, further comprising one or more additional containers selected from the group consisting of:
(a) a container providing a primer hybridizable, under pyrophosphorolysis activated polymerization, to a polynucleotide template;
(b) a container providing a primer having a non-extendable nucleotide at the 3'-terminus, the primer hybridizable, under pyrophosphorolysis activated polymerization conditions, to the polynucleotide template;
(c) a container providing free nucleotides;
(d) a container providing a buffer suitable for pyrophosphorolysis activated polymerization.

* * * * *

SEQUENCE LISTING

<160> NUMBER OF SEQ ID NOS: 60

<210> SEQ ID NO 1
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in -continued region from 3/A subdomain of family A type DNA-dependent
DNA polymerase
<220> FEATURE:
<221> NAME/KEY: MOD_RES
<222> LOCATION: (2)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = any amino acid except Thr
<220> FEATURE:
<221> NAME/KEY: MOD_RES
<222> LOCATION: (11)...(15)
<223> OTHER INFORMATION: Xaa = any amino acid

<400> SEQUENCE: 1

Arg Xaa Xaa Xaa Lys Leu Xaa Xaa Xaa Tyr Xaa Xaa Xaa Xaa Xaa
 1               5                  10                  15

<210> SEQ ID NO 2
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(17)
<223> OTHER INFORMATION: Xaa = any amino acid

<400> SEQUENCE: 2

Xaa Xaa Xaa Xaa Lys Xaa Xaa Xaa Xaa Xaa Xaa Xaa Xaa Xaa Xaa
 1               5                  10                  15

Xaa

<210> SEQ ID NO 3
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus
      thermophilus (Tth)

<400> SEQUENCE: 3

Arg Glu Leu Thr Lys Leu Lys Asn Thr Tyr Val Asp Pro Leu Pro
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus
      caldophilus (Tca)

<400> SEQUENCE: 4

Arg Glu Leu Thr Lys Leu Lys Asn Thr Tyr Val Asp Pro Leu Pro
 1               5                  10                  15

```
<210> SEQ ID NO 5
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus sp. Z05
      (Z05)

<400> SEQUENCE: 5

Arg Glu Leu Thr Lys Leu Lys Asn Thr Tyr Val Asp Pro Leu Pro
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus
      aquaticus (Taq)

<400> SEQUENCE: 6

Arg Glu Leu Thr Lys Leu Lys Ser Thr Tyr Ile Asp Pro Leu Pro
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus flavus
      (Tfl)

<400> SEQUENCE: 7

Arg Glu Leu Thr Lys Leu Lys Asn Thr Tyr Ile Asp Pro Leu Pro
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus
      filiformis (Tfi)

<400> SEQUENCE: 8

Arg Glu Leu Met Lys Leu Lys Ser Thr Tyr Ile Asp Pro Leu Pro
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermus sp.
      sps17 (Sps17)

<400> SEQUENCE: 9

Arg Glu Leu Met Lys Leu Lys Ser Thr Tyr Ile Asp Pro Leu Pro
1               5                   10                  15

<210> SEQ ID NO 10
<211> LENGTH: 15
<212> TYPE: PRT
<213> ORGANISM: Artificial Sequence
```

```
<220> FEATURE:
<223> OTHER INFORMATION: region from 3/A subdomain of family A type
      DNA-dependent DNA polymerase from Deinococcus
      radiodurans (Dra)

<400> SEQUENCE: 10

Arg Glu Leu Asp Lys Leu Arg Gly Thr Tyr Leu Asp Pro Ile Pro
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Hot Spring
      family B/clone 7 (HspB7)

<400> SEQUENCE: 11

Arg Glu Leu Ser Lys Leu Arg Ser Thr Tyr Ala Asp Ala Leu Pro
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Bacillus
      stearothermophilus (Bst)

<400> SEQUENCE: 12

Arg Gln Leu Gly Lys Leu Gln Ser Thr Tyr Ile Glu Gly Leu Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Bacillus
      caldotenax (Bca)

<400> SEQUENCE: 13

Arg Gln Leu Gly Lys Leu Gln Ser Thr Tyr Ile Glu Gly Leu Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Escherichia coli
      (Eco)

<400> SEQUENCE: 14

Arg Gly Leu Ala Lys Leu Lys Ser Thr Tyr Thr Asp Lys Leu Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermotoga
      maritima (Tma)
```

-continued

```
<400> SEQUENCE: 15

Arg Lys Ile Gln Lys Leu Lys Ser Thr Tyr Ile Asp Ala Leu Pro
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermotoga
      neapolitana (Tne)

<400> SEQUENCE: 16

Arg Lys Ile Leu Lys Leu Lys Ser Thr Tyr Ile Asp Thr Leu Pro
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Thermosipho
      africanus (Taf)

<400> SEQUENCE: 17

Arg Lys Tyr Gln Lys Leu Lys Ser Thr Tyr Ile Asp Ser Ile Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: region from 3/A subdomain of family A type
      DNA-dependent DNA polymerase from Hot Spring
      family A (HspA)

<400> SEQUENCE: 18

Arg Thr Leu Ala Lys Leu Lys Ser Thr Tyr Val Asp Ala Leu Pro
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: region from 3/A subdomain of family A type
      DNA-dependent DNA polymerase from Bacteriophage T7
      (T7)

<400> SEQUENCE: 19

Leu Met Ile Gln Lys Arg Ile Gly Gln Ser Ala Glu Gly Asp Lys Ala
1               5                   10                  15

Trp

<210> SEQ ID NO 20
<211> LENGTH: 893
<212> TYPE: PRT
<213> ORGANISM: Artificial Sequence
<220> FEATURE:
<223> OTHER INFORMATION: chimeric CS-family thermostable DNA polymerase
      CS5 with Thermus sp. Z05 N-terminal 5'-nuclease domain
      and Thermotoga maritima C-terminal 3'-5'
      exonuclease and polymerase domains

<400> SEQUENCE: 20
```

-continued

```
Met Lys Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Tyr Lys Ala Val Phe
 50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
355                 360                 365

Lys Leu Lys Glu Ile Leu Glu Asp Pro Gly Ala Lys Ile Val Gly Gln
370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430
```

-continued

```
Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Ile Tyr Arg Ile Ala Gly Glu Pro Phe
            530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly His Glu Ile Ile Pro
                580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
            610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Glu Gly Ile Asp Val His Thr Leu
            690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
```

```
                850                 855                 860
Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 21
<211> LENGTH: 893
<212> TYPE: PRT
<213> ORGANISM: Artificial Sequence
<220> FEATURE:
<223> OTHER INFORMATION: chimeric CS-family thermostable DNA polymerase
      CS6 with Thermus sp. Z05 N-terminal 5'-nuclease domain
      and Thermotoga maritima C-terminal 3'-5'
      exonuclease and polymerase domains

<400> SEQUENCE: 21

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320
```

```
Ala Ile Ala Leu Ala Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
                355                 360                 365

Lys Leu Lys Glu Ile Leu Glu Asp Pro Gly Ala Lys Ile Val Gly Gln
        370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
        530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
        610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
        690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
```

```
                  740                 745                 750
Glu Lys Met Ile Val Asn Tyr Phe Val Leu Tyr Pro Lys Val Arg Asp
                755                 760                 765
Tyr Ile Gln Arg Val Val Ser Glu Ala Lys Glu Lys Gly Tyr Val Arg
            770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                805                 810                 815
Gln Gly Thr Ala Ala Asp Ile Ile Lys Leu Ala Met Ile Glu Ile Asp
                820                 825                 830
Arg Glu Leu Lys Glu Arg Lys Met Arg Ser Lys Met Ile Ile Gln Val
                835                 840                 845
His Asp Glu Leu Val Phe Glu Val Pro Asn Glu Glu Lys Asp Ala Leu
                850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                885                 890
```

<210> SEQ ID NO 22
<211> LENGTH: 2682
<212> TYPE: DNA
<213> ORGANISM: Artificial Sequence
<220> FEATURE:
<223> OTHER INFORMATION: chimeric CS-family thermostable DNA polymerase
  CS5 with Thermus sp. Z05 N-terminal 5'-nuclease domain
  and Thermotoga maritima C-terminal 3'-5'
  exonuclease and polymerase domains

<400> SEQUENCE: 22

```
atgaaagcta tgttaccatt attcgaaccc aaaggccggg tcctcctggt ggacggccac    60
cacctggcct accgcacctt cttcgccctg aagggcctca ccacgagccg ggcgaaccg    120
gtgcaggcgg tttacggctt cgccaagagc ctcctcaagg ccctgaagga ggacgggtac    180
aaggccgtct tcgtggtctt tgacgccaag gccccttcct tccgccacga ggcctacgag    240
gcctacaagg caggccgcgc cccgaccccc gaggacttcc cccggcagct cgccctcatc    300
aaggagctgt ggaccctcct ggggtttact cgcctcgagg ttccgggctt tgaggcggac    360
gacgtcctcg ccaccctggc caagaaggcg gaaagggagg ggtacgaggt gcgcatcctc    420
accgccgacc gggaccttta ccagctcgtc tccgaccgcg tcgccgtcct ccaccccgag    480
ggccacctca tcaccccgga gtggctttgg gagaagtacg gccttaagcc ggagcagtgg    540
gtggacttcc gcgccctcgt ggggaccccc tccgacaacc tcccgggggt caagggcatc    600
ggggagaaga ccgccctcaa gctcctcaag gagtggggaa gcctggaaaa tatcctcaag    660
aacctggacc gggtgaagcc ggaaagcgtc cggaaaagga tcaaggccca cctggaagac    720
cttaagctct ccttggagct ttcccgggtg cgctcggacc tcccctgga ggtggacttc    780
gcccggaggc gggagcctga ccggaaaggg cttcgggcct ttttggagcg cttggagttc    840
ggcagcctcc tccacgagtt cggccttcta gaggagtccg aacccgttgg gtaccgtata    900
gttaaagacc tggttgaatt tgaaaaactc atagagaaac tgagagaatc tccttcgttc    960
gctatcgatt tggaaactag ttccctcgat cctttcgact gcgacattgt cggtatctct   1020
gtgtctttca aaccaaagga agcgtactac ataccactcc atcatagaaa cgcccagaac   1080
ctggacgaaa agaggttct gaaaagctca aagaaattc tggaggaccc cggagcaaag   1140
```

-continued

```
atcgttggtc agaatttgaa attcgattac aaggtgttga tggtgaaggg tgttgaacct    1200
gttcctcctt acttcgacac gatgatacg gcttaccttc ttgagccgaa cgaaaagaag    1260
ttcaatctgg acgatctcgc attgaaattt cttggataca aaatgacatc ttaccaagag    1320
ctcatgtcct tctcttttcc gctgtttggt ttcagttttg ccgatgttcc tgtagaaaaa    1380
gcagcgaact actcctgtga agatgcagac atcacctaca gactttacaa gaccctgagc    1440
ttaaaactcc acgaggcaga tctggaaaac gtgttctaca gatagaaat gccccttgtg    1500 aacgtgcttg cacggatgga actgaacggt gtgtatgtgg acacagagtt cctgaagaaa    1560
ctctcagaag agtacggaaa aaaactcgaa gaactggcag aggaaatata caggatagct    1620
ggagagccgt tcaacataaa ctcaccgaag caggtttcaa ggatcctttt tgaaaaactc    1680
ggcataaaac cacgtggtaa aacgacgaaa acgggagact attcaacacg catagaagtc    1740
ctcgaggaac ttgccggtga acacgaaatc attcctctga ttcttgaata cagaaagata    1800
cagaaattga aatcaaccta catagacgct cttcccaaga tggtcaaccc aaagaccgga    1860
aggattcatg cttctttcaa tcaaacgggg actgccactg gaagacttag cagcagcgat    1920
cccaatcttc agaacctccc gacgaaaagt gaagagggaa aagaaatcag gaaagcgata    1980
gttcctcagg atccaaactg gtggatcgtc agtgccgact actcccaaat gaactgagg     2040 atcctcgccc atctcagtgg tgatgagaat cttttgaggg cattcgaaga gggcatcgac    2100
gtccacactc taacagcttc cagaatattc aacgtgaaac ccgaagaagt aaccgaagaa    2160
atgcgccgcg ctggtaaaat ggttaatttt tccatcatat acggtgtaac accttacggt    2220
ctgtctgtga ggcttggagt acctgtgaaa gaagcagaaa agatgatcgt caactacttc    2280
gtcctctacc caaaggtgcg cgattacatt cagagggtcg tatcggaagc gaaagaaaaa    2340
ggctatgtta gaacgctgtt tggaagaaaa agagacatac cacagctcat ggcccgggac    2400
aggaacacac aggctgaagg gaacgaatt gccataaaca ctcccataca gggtacagca    2460
gcggatataa taaagctggc tatgatagaa atagacaggg aactgaaaga agaaaaatg     2520 agatcgaaga tgatcataca ggtccacgac gaactggttt tgaagtgcc caatgaggaa     2580 aaggacgcgc tcgtcgagct ggtgaaagac agaatgacga atgtggtaaa gctttcagtg    2640
ccgctcgaag tggatgtaac catcggcaaa acatggtcgt ga                       2682
```

<210> SEQ ID NO 23
<211> LENGTH: 2682
<212> TYPE: DNA
<213> ORGANISM: Artificial Sequence
<220> FEATURE:
<223> OTHER INFORMATION: chimeric CS-family thermostable DNA polymerase
      CS6 with Thermus sp. Z05 N-terminal 5'-nuclease domain
      and Thermotoga maritima C-terminal 3'-5'
      exonuclease and polymerase domains

<400> SEQUENCE: 23

```
atgaaagcta tgttaccatt attcgaaccc aaaggccggg tcctcctggt ggacggccac     60
cacctggcct accgcacctt cttcgccctg aagggcctca ccacgagccg ggcgaaccg     120 gtgcaggcgg tttacggctt cgccaagagc ctcctcaagg ccctgaagga ggacgggtac    180
aaggccgtct tcgtggtctt tgacgccaag gccccttcct tccgccacga ggcctacgag    240
gcctacaagg caggccgcgc cccgacccc gaggacttcc cccggcagct cgccctcatc     300
aaggagctgg tggacctcct ggggtttact cgcctcgagg ttccgggctt tgaggcggac    360
gacgtcctcg ccaccctggc caagaaggcg aaagggagg ggtacgaggt gcgcatcctc    420
accgccgacc gggaccttta ccagctcgtc tccgaccgcg tcgccgtcct ccaccccgag    480
```

```
ggccacctca tcaccccgga gtggctttgg gagaagtacg gccttaagcc ggagcagtgg    540
gtggacttcc gcgccctcgt gggggacccc tccgacaacc tccccggggt caagggcatc    600
ggggagaaga ccgccctcaa gctcctcaag gagtggggaa gcctggaaaa tatcctcaag    660
aacctggacc gggtgaagcc ggaaagcgtc cgggaaagga tcaaggccca cctggaagac    720
cttaagctct ccttggagct ttcccgggtg cgctcggacc tcccccctgga ggtggacttc    780 gcccggaggc gggagcctga ccgggaaggg cttcgggcct ttttggagcg cttggagttc    840
ggcagcctcc tccacgagtt cggccttcta gaggagtccg aacccgttgg gtaccgtata    900
gttaaagacc tggttgaatt tgaaaaactc atagagaaac tgagagaatc tccttcgttc    960
gcgatcgctc ttgcgactag ttccctcgat cctttcgact gcgacattgt cggtatctct   1020
gtgtctttca aaccaaagga agcgtactac ataccactcc atcatagaaa cgcccagaac   1080
ctggacgaaa aagaggttct gaaaaagctc aaagaaattc tggaggaccc cggagcaaag   1140
atcgttggtc agaatttgaa attcgattac aaggtgttga tggtgaaggg tgttgaacct   1200
gttcctcctt acttcgacac gatgatagcg gcttaccttc ttgagccgaa cgaaaagaag   1260
ttcaatctgg acgatctcgc attgaaattt cttggataca aaatgacatc ttaccaagag   1320
ctcatgtcct tctcttttcc gctgtttggt ttcagttttg ccgatgttcc tgtagaaaaa   1380
gcagcgaact actcctgtga agatgcagac atcacctaca gacttacaa gaccctgagc   1440 ttaaaactcc acgaggcaga tctggaaaac gtgttctaca agatagaaat gcccttgtg   1500 aacgtgcttg cacggatgga actgaacggt gtgtatgtgg acacagagtt cctgaagaaa   1560
ctctcagaag agtacggaaa aaaactcgaa gaactggcag aggaaatata caggatagct   1620
ggagagccgt tcaacataaa ctcaccgaag caggtttcaa ggatcctttt tgaaaaactc   1680
ggcataaaac cacgtggtaa aacgacgaaa acgggagact attcaacacg catagaagtc   1740
ctcgaggaac ttgccggtga acacgaaatc attcctctga ttcttgaata cagaaagata   1800
cagaaattga aatcaaccta catagacgct cttcccaaga tggtcaaccc aaagaccgga   1860
aggattcatg cttctttcaa tcaaacgggg actgccactg gaagacttag cagcagcgat   1920
cccaatcttc agaacctccc gacgaaaagt gaagagggaa agaaatcag gaaagcgata   1980 gttcctcagg atccaaactg gtggatcgtc agtgccgact actcccaaat gaactgagg    2040 atcctcgccc atctcagtgg tgatgagaat cttttgaggg cattcgaaga gggcatcgac   2100
gtccacactc taacagcttc cagaatattc aacgtgaaac ccgaagaagt aaccgaagaa   2160
atgcgccgcg ctggtaaaat ggttaatttt tccatcatat acggtgtaac accttacggt   2220
ctgtctgtga ggcttggagt acctgtgaaa gaagcagaaa agatgatcgt caactacttc   2280
gtcctctacc caaaggtgcg cgattacatt cagagggtcg tatcggaagc gaaagaaaaa   2340
ggctatgtta gaacgctgtt tggaagaaaa agagacatac cacagctcat ggcccgggac   2400
aggaacacac aggctgaagg agaacgaatt gccataaaca ctcccataca gggtacagca   2460
gcggatataa taaagctggc tatgatagaa atagacaggg aactgaaaga aagaaaaatg   2520
agatcgaaga tgatcataca ggtccacgac gaactggttt ttgaagtgcc caatgaggaa   2580
aaggacgcgc tcgtcgagct ggtgaaagac agaatgacga atgtggtaaa gctttcagtg   2640
ccgctcgaag tggatgtaac catcggcaaa acatggtcgt ga                     2682
```

<210> SEQ ID NO 24
<211> LENGTH: 15
<212> TYPE: PRT
<213> ORGANISM: Artificial Sequence

```
<220> FEATURE:
<223> OTHER INFORMATION: unmodified form of motif in region from 3/A
      subdomain of family A type DNA-dependent DNA
      polymerase
<220> FEATURE:
<221> NAME/KEY: MOD_RES
<222> LOCATION: (2)...(15)
<223> OTHER INFORMATION: Xaa = any amino acid

<400> SEQUENCE: 24

Arg Xaa Xaa Xaa Lys Leu Xaa Xaa Thr Tyr Xaa Xaa Xaa Xaa Xaa
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: unmodified form of motif in region from 3/A
      subdomain of family A type DNA-dependent DNA
      polymerase
<220> FEATURE:
<221> NAME/KEY: MOD_RES
<222> LOCATION: (1)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(17)
<223> OTHER INFORMATION: Xaa = any amino acid

<400> SEQUENCE: 25

Xaa Xaa Xaa Xaa Lys Xaa Xaa Xaa Xaa Xaa Xaa Xaa Xaa Xaa Xaa
1               5                   10                  15

Xaa

<210> SEQ ID NO 26
<211> LENGTH: 22
<212> TYPE: DNA
<213> ORGANISM: Artificial Sequence
<220> FEATURE:
<223> OTHER INFORMATION: synthetic KAB77 primer for pyrophosphorolysis
      activated polymerization (PAP-PCR) model system
      using M13mp18 template
<220> FEATURE:
<221> NAME/KEY: modified_base
<222> LOCATION: (22)...(22)
<223> OTHER INFORMATION: n = 2'-phosphate-deoxyadenosine

<400> SEQUENCE: 26
cgcctggtct gtacaccgtt cn                                              22

<210> SEQ ID NO 27
<211> LENGTH: 24
<212> TYPE: DNA
<213> ORGANISM: Artificial Sequence
<220> FEATURE:
<223> OTHER INFORMATION: synthetic KAB71 primer for pyrophosphorolysis
      activated polymerization (PAP-PCR) model system
      using M13mp18 template
<220> FEATURE:
<221> NAME/KEY: modified_base
<222> LOCATION: (24)...(24)
<223> OTHER INFORMATION: n = 2'-phosphate-deoxyadenosine

<400> SEQUENCE: 27
ggaacgaggg tagcaacggc tacn                                            24
```

```
<210> SEQ ID NO 28
<211> LENGTH: 15
<212> TYPE: PRT
<213> ORGANISM: Artificial Sequence
<220> FEATURE:
<223> OTHER INFORMATION: region from 3/A subdomain of chimeric CS-family
      thermostable DNA polymerase from CS5

<400> SEQUENCE: 28

Arg Lys Ile Gln Lys Leu Lys Ser Thr Tyr Ile Asp Ala Leu Pro
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: region from 3/A subdomain of chimeric CS-family
      thermostable DNA polymerase from CS6

<400> SEQUENCE: 29

Arg Lys Ile Gln Lys Leu Lys Ser Thr Tyr Ile Asp Ala Leu Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: consensus sequence for region from 3/A
      subdomain of family A type DNA-dependent DNA polymerase
<220> FEATURE:
<221> NAME/KEY: MOD_RES
<222> LOCATION: (2)...(4)
<223> OTHER INFORMATION: Xaa = any amino acid
<220> FEATURE:
<221> NAME/KEY: MOD_RES
<222> LOCATION: (7)...(7)
<223> OTHER INFORMATION: Xaa = Ile or absent
<220> FEATURE:
<221> NAME/KEY: MOD_RES
<222> LOCATION: (8)...(8)
<223> OTHER INFORMATION: Xaa = Gly or absent
<220> FEATURE:
<221> NAME/KEY: MOD_RES
<222> LOCATION: (9)...(16)
<223> OTHER INFORMATION: Xaa = any amino acid

<400> SEQUENCE: 30

Arg Xaa Xaa Xaa Lys Leu Xaa Xaa Xaa Xaa Thr Tyr Xaa Xaa Xaa Xaa
1               5                   10                  15

<210> SEQ ID NO 31
<211> LENGTH: 20
<212> TYPE: DNA
<213> ORGANISM: Artificial Sequence
<220> FEATURE:
<223> OTHER INFORMATION: synthetic error-prone PCR amplification
      forward primer

<400> SEQUENCE: 31
gcagcgaact actcctgtga                                              20

<210> SEQ ID NO 32
<211> LENGTH: 23
<212> TYPE: DNA
<213> ORGANISM: Artificial Sequence
<220> FEATURE:
<223> OTHER INFORMATION: synthetic error-prone PCR amplification
      reverse primer

<400> SEQUENCE: 32
```
acatccactt cgagcggcac tga                                              23

<210> SEQ ID NO 33
<211> LENGTH: 30
<212> TYPE: DNA
<213> ORGANISM: Artificial Sequence
<220> FEATURE:
<223> OTHER INFORMATION: synthetic M13mp18 single-stranded DNA
      template oligonucleotide primer

<400> SEQUENCE: 33
gggaagggcg atcggtgcgg gcctcttcgc                                       30

<210> SEQ ID NO 34
<211> LENGTH: 22
<212> TYPE: DNA
<213> ORGANISM: Artificial Sequence
<220> FEATURE:
<223> OTHER INFORMATION: synthetic pre-annealed oligo duplex
      substrate primer strand
<220> FEATURE:
<221> NAME/KEY: modified_base
<222> LOCATION: (22)...(22)
<223> OTHER INFORMATION: n = 2'-phosphate-deoxyadenosine

<400> SEQUENCE: 34
cgcctggtct gtacaccgtt cn                                               22

<210> SEQ ID NO 35
<211> LENGTH: 42
<212> TYPE: DNA
<213> ORGANISM: Artificial Sequence
<220> FEATURE:
<223> OTHER INFORMATION: synthetic pre-annealed oligo duplex
      substrate template strand
<220> FEATURE:
<221> NAME/KEY: modified_base
<222> LOCATION: (29)...(39)
<223> OTHER INFORMATION: n = 7-deaza-deoxyguanosine
<220> FEATURE:
<221> NAME/KEY: modified_base
<222> LOCATION: (42)...(42)
<223> OTHER INFORMATION: g modified by 3'-phosphate

<400> SEQUENCE: 35
caactttgaa agaggacaga tgaacggtnt acanaccang cg                         42

<210> SEQ ID NO 36
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(2)
<223> OTHER INFORMATION: Xaa = any amino acid
<220> FEATURE:
<221> NAME/KEY: MOD_RES
<222> LOCATION: (3)...(3)
<223> OTHER INFORMATION: Xaa = Leu, Ile or Tyr
<220> FEATURE:
<221> NAME/KEY: MOD_RES
<222> LOCATION: (4)...(4)
<223> OTHER INFORMATION: Xaa = any amino acid
<220> FEATURE:
<221> NAME/KEY: MOD_RES
<222> LOCATION: (7)...(7)
<223> OTHER INFORMATION: Xaa = Lys, Arg or Gln

```
<220> FEATURE:
<221> NAME/KEY: MOD_RES
<222> LOCATION: (8)...(8)
<223> OTHER INFORMATION: Xaa = Asn, Ser or Gly
<220> FEATURE:
<221> NAME/KEY: MOD_RES
<222> LOCATION: (9)...(9)
<223> OTHER INFORMATION: Xaa = any amino acid except Thr
<220> FEATURE:
<221> NAME/KEY: MOD_RES
<222> LOCATION: (11)...(11)
<223> OTHER INFORMATION: Xaa = any amino acid
<220> FEATURE:
<221> NAME/KEY: MOD_RES
<222> LOCATION: (12)...(12)
<223> OTHER INFORMATION: Xaa = Asp or Glu
<220> FEATURE:
<221> NAME/KEY: MOD_RES
<222> LOCATION: (13)...(13)
<223> OTHER INFORMATION: Xaa = any amino acid
<220> FEATURE:
<221> NAME/KEY: MOD_RES
<222> LOCATION: (14)...(14)
<223> OTHER INFORMATION: Xaa = Leu or Ile
<220> FEATURE:
<221> NAME/KEY: MOD_RES
<222> LOCATION: (15)...(15)
<223> OTHER INFORMATION: Xaa = Pro or Leu

<400> SEQUENCE: 36

Arg Xaa Xaa Xaa Lys Leu Xaa Xaa Xaa Tyr Xaa Xaa Xaa Xaa Xaa
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: modified motif having improved
     pyrophosphorolysis activated polymerization (PAP) ability in
     region from 3/A subdomain of family A type DNA-dependent
     DNA polymerase
<220> FEATURE:
<221> NAME/KEY: MOD_RES
<222> LOCATION: (2)...(2)
<223> OTHER INFORMATION: Xaa = Glu, Gln, Lys or Thr
<220> FEATURE:
<221> NAME/KEY: MOD_RES
<222> LOCATION: (3)...(3)
<223> OTHER INFORMATION: Xaa = any amino acid
<220> FEATURE:
<221> NAME/KEY: MOD_RES
<222> LOCATION: (4)...(4)
<223> OTHER INFORMATION: Xaa = Thr, Met, Asp, Ser, Gly, Ala, Gln or Leu
<220> FEATURE:
<221> NAME/KEY: MOD_RES
<222> LOCATION: (7)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = any amino acid except Thr
<220> FEATURE:
<221> NAME/KEY: MOD_RES
<222> LOCATION: (11)...(11)
<223> OTHER INFORMATION: Xaa = Val, Ile, Leu, Ala or Thr
<220> FEATURE:
<221> NAME/KEY: MOD_RES
<222> LOCATION: (12)...(12)
<223> OTHER INFORMATION: Xaa = any amino acid
<220> FEATURE:
<221> NAME/KEY: MOD_RES
<222> LOCATION: (13)...(13)
<223> OTHER INFORMATION: Xaa = Pro, Ala, Gly, Lys, Thr or Ser
<220> FEATURE:
<221> NAME/KEY: MOD_RES
<222> LOCATION: (14)...(15)
<223> OTHER INFORMATION: Xaa = any amino acid
```

-continued

<400> SEQUENCE: 37

Arg Xaa Xaa Xaa Lys Leu Xaa Xaa Xaa Tyr Xaa Xaa Xaa Xaa Xaa
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = Gly, Ala, Leu, Met, Phe, Trp, Lys, Gln,
      Glu, Ser, Pro, Val, Ile, Cys, Tyr, His, Arg, Asn or Asp
<220> FEATURE:
<221> NAME/KEY: MOD_RES
<222> LOCATION: (11)...(15)
<223> OTHER INFORMATION: Xaa = any amino acid

<400> SEQUENCE: 38

Arg Xaa Xaa Xaa Lys Leu Xaa Xaa Xaa Tyr Xaa Xaa Xaa Xaa Xaa
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(15)
<223> OTHER INFORMATION: Xaa = any amino acid

<400> SEQUENCE: 39

Arg Xaa Xaa Xaa Lys Leu Xaa Xaa Ser Tyr Xaa Xaa Xaa Xaa Xaa
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(1)
<223> OTHER INFORMATION: Xaa = Arg or Leu
<220> FEATURE:
<221> NAME/KEY: MOD_RES
<222> LOCATION: (2)...(2)
<223> OTHER INFORMATION: Xaa = any amino acid
<220> FEATURE:
<221> NAME/KEY: MOD_RES
<222> LOCATION: (3)...(3)
<223> OTHER INFORMATION: Xaa = Leu, Ile or Tyr
<220> FEATURE:
<221> NAME/KEY: MOD_RES
<222> LOCATION: (4)...(4)

-continued

```
<223> OTHER INFORMATION: Xaa = any amino acid
<220> FEATURE:
<221> NAME/KEY: MOD_RES
<222> LOCATION: (6)...(6)
<223> OTHER INFORMATION: Xaa = Arg or Leu
<220> FEATURE:
<221> NAME/KEY: MOD_RES
<222> LOCATION: (7)...(7)
<223> OTHER INFORMATION: Xaa = Ile or absent
<220> FEATURE:
<221> NAME/KEY: MOD_RES
<222> LOCATION: (8)...(8)
<223> OTHER INFORMATION: Xaa = Gly or absent
<220> FEATURE:
<221> NAME/KEY: MOD_RES
<222> LOCATION: (9)...(9)
<223> OTHER INFORMATION: Xaa = Lys, Arg or Gln
<220> FEATURE:
<221> NAME/KEY: MOD_RES
<222> LOCATION: (10)...(10)
<223> OTHER INFORMATION: Xaa = Asn, Ser or Gly
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(12)
<223> OTHER INFORMATION: Xaa = Tyr or Glu
<220> FEATURE:
<221> NAME/KEY: MOD_RES
<222> LOCATION: (13)...(13)
<223> OTHER INFORMATION: Xaa = any amino acid
<220> FEATURE:
<221> NAME/KEY: MOD_RES
<222> LOCATION: (14)...(14)
<223> OTHER INFORMATION: Xaa = Asp or Glu
<220> FEATURE:
<221> NAME/KEY: MOD_RES
<222> LOCATION: (15)...(15)
<223> OTHER INFORMATION: Xaa = any amino acid
<220> FEATURE:
<221> NAME/KEY: MOD_RES
<222> LOCATION: (16)...(16)
<223> OTHER INFORMATION: Xaa = Leu, Ile or Ala
<220> FEATURE:
<221> NAME/KEY: MOD_RES
<222> LOCATION: (17)...(17)
<223> OTHER INFORMATION: Xaa = Pro, Leu or Trp

<400> SEQUENCE: 40

Xaa Xaa Xaa Xaa Lys Xaa Xaa Xaa Xaa Xaa Xaa Xaa Xaa Xaa Xaa Xaa
 1               5                   10                  15

Xaa

<210> SEQ ID NO 41
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(1)
<223> OTHER INFORMATION: Xaa = any amino acid
<220> FEATURE:
<221> NAME/KEY: MOD_RES
<222> LOCATION: (2)...(2)
<223> OTHER INFORMATION: Xaa = Glu, Gln, Gly, Lys, Thr or Met
<220> FEATURE:
<221> NAME/KEY: MOD_RES
<222> LOCATION: (3)...(3)
<223> OTHER INFORMATION: Xaa = any amino acid
<220> FEATURE:
```

```
<221> NAME/KEY: MOD_RES
<222> LOCATION: (4)...(4)
<223> OTHER INFORMATION: Xaa = Thr, Met, Asp, Ser, Gly, Ala, Gln or Leu
<220> FEATURE:
<221> NAME/KEY: MOD_RES
<222> LOCATION: (6)...(12)
<223> OTHER INFORMATION: Xaa = any amino acid
<220> FEATURE:
<221> NAME/KEY: MOD_RES
<222> LOCATION: (13)...(13)
<223> OTHER INFORMATION: Xaa = Val, Ile, Leu, Ala, Thr or Gly
<220> FEATURE:
<221> NAME/KEY: MOD_RES
<222> LOCATION: (14)...(14)
<223> OTHER INFORMATION: Xaa = any amino acid
<220> FEATURE:
<221> NAME/KEY: MOD_RES
<222> LOCATION: (15)...(15)
<223> OTHER INFORMATION: Xaa = Pro, Ala, Gly, Lys, Thr or Ser
<220> FEATURE:
<221> NAME/KEY: MOD_RES
<222> LOCATION: (16)...(17)
<223> OTHER INFORMATION: Xaa = any amino acid

<400> SEQUENCE: 41

Xaa Xaa Xaa Xaa Lys Xaa Xaa Xaa Xaa Xaa Xaa Xaa Xaa Xaa Xaa Xaa
 1               5                   10                  15

Xaa

<210> SEQ ID NO 42
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = Gly, Leu, Met, Phe, Trp, Lys, Gln, Glu,
      Ser, Pro, Val, Ile, Cys, Tyr, His, Arg, Asn or Asp
<220> FEATURE:
<221> NAME/KEY: MOD_RES
<222> LOCATION: (12)...(17)
<223> OTHER INFORMATION: Xaa = any amino acid

<400> SEQUENCE: 42

Xaa Xaa Xaa Xaa Lys Xaa Xaa Xaa Xaa Xaa Xaa Xaa Xaa Xaa Xaa Xaa
 1               5                   10                  15

Xaa

<210> SEQ ID NO 43
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(17)
<223> OTHER INFORMATION: Xaa = any amino acid

<400> SEQUENCE: 43

Xaa Xaa Xaa Xaa Lys Xaa Xaa Xaa Xaa Xaa Ser Xaa Xaa Xaa Xaa Xaa
```

```
1               5                  10                  15
Xaa

<210> SEQ ID NO 44
<211> LENGTH: 15
<212> TYPE: PRT
<213> ORGANISM: Artificial Sequence
<220> FEATURE:
<223> OTHER INFORMATION: unmodified motif region from 3/A subdomain of
      family A type DNA-dependent DNA polymerase
<220> FEATURE:
<221> NAME/KEY: MOD_RES
<222> LOCATION: (2)...(2)
<223> OTHER INFORMATION: Xaa = any amino acid
<220> FEATURE:
<221> NAME/KEY: MOD_RES
<222> LOCATION: (3)...(3)
<223> OTHER INFORMATION: Xaa = Leu, Ile or Tyr
<220> FEATURE:
<221> NAME/KEY: MOD_RES
<222> LOCATION: (4)...(4)
<223> OTHER INFORMATION: Xaa = any amino acid
<220> FEATURE:
<221> NAME/KEY: MOD_RES
<222> LOCATION: (7)...(7)
<223> OTHER INFORMATION: Xaa = Lys, Arg or Gln
<220> FEATURE:
<221> NAME/KEY: MOD_RES
<222> LOCATION: (8)...(8)
<223> OTHER INFORMATION: Xaa = Asn, Ser or Gly
<220> FEATURE:
<221> NAME/KEY: MOD_RES
<222> LOCATION: (11)...(11)
<223> OTHER INFORMATION: Xaa = any amino acid
<220> FEATURE:
<221> NAME/KEY: MOD_RES
<222> LOCATION: (12)...(12)
<223> OTHER INFORMATION: Xaa = Asp or Glu
<220> FEATURE:
<221> NAME/KEY: MOD_RES
<222> LOCATION: (13)...(13)
<223> OTHER INFORMATION: Xaa = any amino acid
<220> FEATURE:
<221> NAME/KEY: MOD_RES
<222> LOCATION: (14)...(14)
<223> OTHER INFORMATION: Xaa = Leu or Ile
<220> FEATURE:
<221> NAME/KEY: MOD_RES
<222> LOCATION: (15)...(15)
<223> OTHER INFORMATION: Xaa = Pro or Leu

<400> SEQUENCE: 44

Arg Xaa Xaa Xaa Lys Leu Xaa Xaa Thr Tyr Xaa Xaa Xaa Xaa Xaa
1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(2)
<223> OTHER INFORMATION: Xaa = Glu, Gln, Gly, Lys or Thr
<220> FEATURE:
<221> NAME/KEY: MOD_RES
<222> LOCATION: (3)...(3)
<223> OTHER INFORMATION: Xaa = any amino acid
<220> FEATURE:
<221> NAME/KEY: MOD_RES
<222> LOCATION: (4)...(4)
<223> OTHER INFORMATION: Xaa = Thr, Met, Asp, Ser, Gly, Ala, Gln or Leu
```

```
<220> FEATURE:
<221> NAME/KEY: MOD_RES
<222> LOCATION: (7)...(8)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = Val, Ile, Leu, Ala or Thr
<220> FEATURE:
<221> NAME/KEY: MOD_RES
<222> LOCATION: (12)...(12)
<223> OTHER INFORMATION: Xaa = any amino acid
<220> FEATURE:
<221> NAME/KEY: MOD_RES
<222> LOCATION: (13)...(13)
<223> OTHER INFORMATION: Xaa = Pro, Ala, Gly, Lys, Thr or Ser
<220> FEATURE:
<221> NAME/KEY: MOD_RES
<222> LOCATION: (14)...(15)
<223> OTHER INFORMATION: Xaa = any amino acid

<400> SEQUENCE: 45

Arg Xaa Xaa Xaa Lys Leu Xaa Xaa Thr Tyr Xaa Xaa Xaa Xaa Xaa
 1               5                  10                  15

<210> SEQ ID NO 46
<211> LENGTH: 15
<212> TYPE: PRT
<213> ORGANISM: Artificial Sequence
<220> FEATURE:
<223> OTHER INFORMATION: modified motif having improved
     pyrophosphorolysis activated polymerization (PAP) ability in
     region from 3/A subdomain of family A type DNA-dependent
     DNA polymerase
<220> FEATURE:
<221> NAME/KEY: MOD_RES
<222> LOCATION: (2)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = Gly, Ala, Leu, Met, Phe, Trp, Lys, Gln,
     Glu, Ser, Pro, Val, Ile, Cys, Tyr, His, Arg, Asn or Asp
<220> FEATURE:
<221> NAME/KEY: MOD_RES
<222> LOCATION: (11)...(15)
<223> OTHER INFORMATION: Xaa = any amino acid

<400> SEQUENCE: 46

Arg Xaa Xaa Xaa Lys Leu Xaa Xaa Xaa Tyr Xaa Xaa Xaa Xaa Xaa
 1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: modified motif having improved
     pyrophosphorolysis activated polymerization (PAP) ability in
     region from 3/A subdomain of family A type DNA-dependent
     DNA polymerase
<220> FEATURE:
<221> NAME/KEY: MOD_RES
<222> LOCATION: (2)...(15)
<223> OTHER INFORMATION: Xaa = any amino acid

<400> SEQUENCE: 47

Arg Xaa Xaa Xaa Lys Leu Xaa Xaa Ser Tyr Xaa Xaa Xaa Xaa Xaa
 1               5                  10                  15

<210> SEQ ID NO 48
<211> LENGTH: 17
<212> TYPE: PRT
<213> ORGANISM: Artificial Sequence
```

```
<220> FEATURE:
<223> OTHER INFORMATION: unmodified motif region from 3/A subdomain of
      family A type DNA-dependent DNA polymerase
<220> FEATURE:
<221> NAME/KEY: MOD_RES
<222> LOCATION: (1)...(1)
<223> OTHER INFORMATION: Xaa = Arg or Leu
<220> FEATURE:
<221> NAME/KEY: MOD_RES
<222> LOCATION: (2)...(2)
<223> OTHER INFORMATION: Xaa = any amino acid
<220> FEATURE:
<221> NAME/KEY: MOD_RES
<222> LOCATION: (3)...(3)
<223> OTHER INFORMATION: Xaa = Leu, Ile or Tyr
<220> FEATURE:
<221> NAME/KEY: MOD_RES
<222> LOCATION: (4)...(4)
<223> OTHER INFORMATION: Xaa = any amino acid
<220> FEATURE:
<221> NAME/KEY: MOD_RES
<222> LOCATION: (6)...(6)
<223> OTHER INFORMATION: Xaa = Arg or Leu
<220> FEATURE:
<221> NAME/KEY: MOD_RES
<222> LOCATION: (7)...(7)
<223> OTHER INFORMATION: Xaa = Ile or absent
<220> FEATURE:
<221> NAME/KEY: MOD_RES
<222> LOCATION: (8)...(8)
<223> OTHER INFORMATION: Xaa = Gly or absent
<220> FEATURE:
<221> NAME/KEY: MOD_RES
<222> LOCATION: (9)...(9)
<223> OTHER INFORMATION: Xaa = Lys, Arg or Gln
<220> FEATURE:
<221> NAME/KEY: MOD_RES
<222> LOCATION: (10)...(10)
<223> OTHER INFORMATION: Xaa = Asn, Ser or Gly
<220> FEATURE:
<221> NAME/KEY: MOD_RES
<222> LOCATION: (11)...(11)
<223> OTHER INFORMATION: Xaa = Thr or Ala
<220> FEATURE:
<221> NAME/KEY: MOD_RES
<222> LOCATION: (12)...(12)
<223> OTHER INFORMATION: Xaa = Tyr or Glu
<220> FEATURE:
<221> NAME/KEY: MOD_RES
<222> LOCATION: (13)...(13)
<223> OTHER INFORMATION: Xaa = any amino acid
<220> FEATURE:
<221> NAME/KEY: MOD_RES
<222> LOCATION: (14)...(14)
<223> OTHER INFORMATION: Xaa = Asp or Glu
<220> FEATURE:
<221> NAME/KEY: MOD_RES
<222> LOCATION: (15)...(15)
<223> OTHER INFORMATION: Xaa = any amino acid
<220> FEATURE:
<221> NAME/KEY: MOD_RES
<222> LOCATION: (16)...(16)
<223> OTHER INFORMATION: Xaa = Leu, Ile or Ala
<220> FEATURE:
<221> NAME/KEY: MOD_RES
<222> LOCATION: (17)...(17)
<223> OTHER INFORMATION: Xaa = Pro, Leu or Trp

<400> SEQUENCE: 48

Xaa Xaa Xaa Xaa Lys Xaa Xaa Xaa Xaa Xaa Xaa Xaa Xaa Xaa Xaa Xaa
1               5                   10                  15

Xaa

<210> SEQ ID NO 49
<211> LENGTH: 17
<212> TYPE: PRT
<213> ORGANISM: Artificial Sequence
```

```
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(1)
<223> OTHER INFORMATION: Xaa = any amino acid
<220> FEATURE:
<221> NAME/KEY: MOD_RES
<222> LOCATION: (2)...(2)
<223> OTHER INFORMATION: Xaa = Glu, Gln, Gly, Lys, Thr or Met
<220> FEATURE:
<221> NAME/KEY: MOD_RES
<222> LOCATION: (3)...(3)
<223> OTHER INFORMATION: Xaa = any amino acid
<220> FEATURE:
<221> NAME/KEY: MOD_RES
<222> LOCATION: (4)...(4)
<223> OTHER INFORMATION: Xaa = Thr, Met, Asp, Ser, Gly, Ala, Gln or Leu
<220> FEATURE:
<221> NAME/KEY: MOD_RES
<222> LOCATION: (6)...(12)
<223> OTHER INFORMATION: Xaa = any amino acid
<220> FEATURE:
<221> NAME/KEY: MOD_RES
<222> LOCATION: (13)...(13)
<223> OTHER INFORMATION: Xaa = Val, Ile, Leu, Ala, Thr or Gly
<220> FEATURE:
<221> NAME/KEY: MOD_RES
<222> LOCATION: (14)...(14)
<223> OTHER INFORMATION: Xaa = any amino acid
<220> FEATURE:
<221> NAME/KEY: MOD_RES
<222> LOCATION: (15)...(15)
<223> OTHER INFORMATION: Xaa = Pro, Ala, Gly, Lys, Thr or Ser
<220> FEATURE:
<221> NAME/KEY: MOD_RES
<222> LOCATION: (16)...(17)
<223> OTHER INFORMATION: Xaa = any amino acid

<400> SEQUENCE: 49

Xaa Xaa Xaa Xaa Lys Xaa Xaa Xaa Xaa Xaa Xaa Xaa Xaa Xaa Xaa Xaa
 1               5                  10                  15

Xaa

<210> SEQ ID NO 50
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = Gly, Leu, Met, Phe, Trp, Lys, Gln, Glu,
      Ser, Pro, Val, Ile, Cys, Tyr, His, Arg, Asn or Asp
<220> FEATURE:
<221> NAME/KEY: MOD_RES
<222> LOCATION: (12)...(17)
<223> OTHER INFORMATION: Xaa = any amino acid

<400> SEQUENCE: 50

Xaa Xaa Xaa Xaa Lys Xaa Xaa Xaa Xaa Xaa Xaa Xaa Xaa Xaa Xaa Xaa
 1               5                  10                  15

Xaa
```

```
<210> SEQ ID NO 51
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(17)
<223> OTHER INFORMATION: Xaa = any amino acid

<400> SEQUENCE: 51

Xaa Xaa Xaa Xaa Lys Xaa Xaa Xaa Xaa Xaa Ser Xaa Xaa Xaa Xaa
 1               5                  10                  15

Xaa

<210> SEQ ID NO 52
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(2)
<223> OTHER INFORMATION: Xaa = Glu, Gln, Gly, Lys or Thr
<220> FEATURE:
<221> NAME/KEY: MOD_RES
<222> LOCATION: (3)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = any amino acid except Thr
<220> FEATURE:
<221> NAME/KEY: MOD_RES
<222> LOCATION: (11)...(15)
<223> OTHER INFORMATION: Xaa = any amino acid

<400> SEQUENCE: 52

Arg Xaa Xaa Xaa Lys Leu Xaa Xaa Xaa Tyr Xaa Xaa Xaa Xaa Xaa
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(3)
<223> OTHER INFORMATION: Xaa = any amino acid
<220> FEATURE:
<221> NAME/KEY: MOD_RES
<222> LOCATION: (4)...(4)
<223> OTHER INFORMATION: Xaa = Thr, Met, Asp, Ser, Gly, Ala, Gln or Leu
<220> FEATURE:
<221> NAME/KEY: MOD_RES
<222> LOCATION: (7)...(15)
<223> OTHER INFORMATION: Xaa = any amino acid

<400> SEQUENCE: 53

Arg Xaa Xaa Xaa Lys Leu Xaa Xaa Xaa Tyr Xaa Xaa Xaa Xaa Xaa
```

<210> SEQ ID NO 54
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = any amino acid except Thr
<220> FEATURE:
<221> NAME/KEY: MOD_RES
<222> LOCATION: (11)...(11)
<223> OTHER INFORMATION: Xaa = Val, Ile, Leu, Ala or Thr
<220> FEATURE:
<221> NAME/KEY: MOD_RES
<222> LOCATION: (12)...(15)
<223> OTHER INFORMATION: Xaa = any amino acid

<400> SEQUENCE: 54

Arg Xaa Xaa Xaa Lys Leu Xaa Xaa Xaa Tyr Xaa Xaa Xaa Xaa Xaa
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(8)
<223> OTHER INFORMATION: Xaa = any amino acid
<220> FEATURE:
<221> NAME/KEY: MOD_RES
<222> LOCATION: (9)...(9)
<223> OTHER INFORMATION: Xaa = any amino acid except Thr
<220> FEATURE:
<221> NAME/KEY: MOD_RES
<222> LOCATION: (11)...(12)
<223> OTHER INFORMATION: Xaa = any amino acid
<220> FEATURE:
<221> NAME/KEY: MOD_RES
<222> LOCATION: (13)...(13)
<223> OTHER INFORMATION: Xaa = Pro, Ala, Gly, Lys, Thr or Ser
<220> FEATURE:
<221> NAME/KEY: MOD_RES
<222> LOCATION: (14)...(15)
<223> OTHER INFORMATION: Xaa = any amino acid

<400> SEQUENCE: 55

Arg Xaa Xaa Xaa Lys Leu Xaa Xaa Xaa Tyr Xaa Xaa Xaa Xaa Xaa
 1               5                  10                  15

<210> SEQ ID NO 56
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase

```
<220> FEATURE:
<221> NAME/KEY: MOD_RES
<222> LOCATION: (1)...(1)
<223> OTHER INFORMATION: Xaa = any amino acid
<220> FEATURE:
<221> NAME/KEY: MOD_RES
<222> LOCATION: (2)...(2)
<223> OTHER INFORMATION: Xaa = Glu, Gln, Gly, Lys, Thr or Met
<220> FEATURE:
<221> NAME/KEY: MOD_RES
<222> LOCATION: (3)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(17)
<223> OTHER INFORMATION: Xaa = any amino acid

<400> SEQUENCE: 56

Xaa Xaa Xaa Xaa Lys Xaa Xaa Xaa Xaa Xaa Xaa Xaa Xaa Xaa Xaa Xaa
 1               5                  10                  15

Xaa

<210> SEQ ID NO 57
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(3)
<223> OTHER INFORMATION: Xaa = any amino acid
<220> FEATURE:
<221> NAME/KEY: MOD_RES
<222> LOCATION: (4)...(4)
<223> OTHER INFORMATION: Xaa = Thr, Met, Asp, Ser, Gly, Ala, Gln or Leu
<220> FEATURE:
<221> NAME/KEY: MOD_RES
<222> LOCATION: (6)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(17)
<223> OTHER INFORMATION: Xaa = any amino acid

<400> SEQUENCE: 57

Xaa Xaa Xaa Xaa Lys Xaa Xaa Xaa Xaa Xaa Xaa Xaa Xaa Xaa Xaa Xaa
 1               5                  10                  15

Xaa

<210> SEQ ID NO 58
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(10)
<223> OTHER INFORMATION: Xaa = any amino acid
```

```
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(12)
<223> OTHER INFORMATION: Xaa = any amino acid
<220> FEATURE:
<221> NAME/KEY: MOD_RES
<222> LOCATION: (13)...(13)
<223> OTHER INFORMATION: Xaa = Val, Ile, Leu, Ala, Thr or Gly
<220> FEATURE:
<221> NAME/KEY: MOD_RES
<222> LOCATION: (14)...(17)
<223> OTHER INFORMATION: Xaa = any amino acid

<400> SEQUENCE: 58

Xaa Xaa Xaa Xaa Lys Xaa Xaa Xaa Xaa Xaa Xaa Xaa Xaa Xaa Xaa Xaa
 1               5                  10                  15

Xaa

<210> SEQ ID NO 59
<211> LENGTH: 17
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (1)...(10)
<223> OTHER INFORMATION: Xaa = any amino acid
<220> FEATURE:
<221> NAME/KEY: MOD_RES
<222> LOCATION: (11)...(11)
<223> OTHER INFORMATION: Xaa = any amino acid except Thr or Ala
<220> FEATURE:
<221> NAME/KEY: MOD_RES
<222> LOCATION: (12)...(14)
<223> OTHER INFORMATION: Xaa = any amino acid
<220> FEATURE:
<221> NAME/KEY: MOD_RES
<222> LOCATION: (15)...(15)
<223> OTHER INFORMATION: Xaa = Pro, Ala, Gly, Lys, Thr or Ser
<220> FEATURE:
<221> NAME/KEY: MOD_RES
<222> LOCATION: (16)...(17)
<223> OTHER INFORMATION: Xaa = any amino acid

<400> SEQUENCE: 59

Xaa Xaa Xaa Xaa Lys Xaa Xaa Xaa Xaa Xaa Xaa Xaa Xaa Xaa Xaa Xaa
 1               5                  10                  15

Xaa

<210> SEQ ID NO 60
<211> LENGTH: 15
<212> TYPE: PRT
<213> ORGANISM: Artificial Sequence
<220> FEATURE:
<223> OTHER INFORMATION: modified motif having improved
      pyrophosphorolysis activated polymerization (PAP) ability in
      region from 3/A subdomain of family A type DNA-dependent
      DNA polymerase
<220> FEATURE:
<221> NAME/KEY: MOD_RES
<222> LOCATION: (2)...(2)
<223> OTHER INFORMATION: Xaa = Glu, Gln, Gly, Lys or Thr
<220> FEATURE:
<221> NAME/KEY: MOD_RES
<222> LOCATION: (3)...(3)
<223> OTHER INFORMATION: Xaa = Leu, Ile or Tyr
```

```
<220> FEATURE:
<221> NAME/KEY: MOD_RES
<222> LOCATION: (4)...(4)
<223> OTHER INFORMATION: Xaa = Thr, Met, Asp, Ser, Gly, Ala, Gln or Leu
<220> FEATURE:
<221> NAME/KEY: MOD_RES
<222> LOCATION: (7)...(7)
<223> OTHER INFORMATION: Xaa = Lys, Arg or Gln
<220> FEATURE:
<221> NAME/KEY: MOD_RES
<222> LOCATION: (8)...(8)
<223> OTHER INFORMATION: Xaa = Asn, Ser or Gly
<220> FEATURE:
<221> NAME/KEY: MOD_RES
<222> LOCATION: (11)...(11)
<223> OTHER INFORMATION: Xaa = Val, Ile, Leu, Ala or Thr
<220> FEATURE:
<221> NAME/KEY: MOD_RES
<222> LOCATION: (12)...(12)
<223> OTHER INFORMATION: Xaa = Asp or Glu
<220> FEATURE:
<221> NAME/KEY: MOD_RES
<222> LOCATION: (13)...(13)
<223> OTHER INFORMATION: Xaa = Pro, Ala, Gly, Lys, Thr or Ser
<220> FEATURE:
<221> NAME/KEY: MOD_RES
<222> LOCATION: (14)...(14)
<223> OTHER INFORMATION: Xaa = Leu or Ile
<220> FEATURE:
<221> NAME/KEY: MOD_RES
<222> LOCATION: (15)...(15)
<223> OTHER INFORMATION: Xaa = Pro or Leu

<400> SEQUENCE: 60

Arg Xaa Xaa Xaa Lys Leu Xaa Xaa Ser Tyr Xaa Xaa Xaa Xaa Xaa
 1               5                  10                  15
```